US008208601B2

(12) United States Patent
Comer et al.

(10) Patent No.: US 8,208,601 B2
(45) Date of Patent: Jun. 26, 2012

(54) INTEGRATED SHAPING AND SCULPTING UNIT FOR USE WITH INTENSITY MODULATED RADIATION THERAPY (IMRT) TREATMENT

(75) Inventors: Sean Comer, Helotes, TX (US); Johnie McConnaughhay, Greenvile, SC (US); George F. Schroeder, San Antonio, TX (US)

(73) Assignee: Oncology Tech LLC, San Antonio, TX (US)

( * ) Notice: Subject to any disclaimer, the term of this patent is extended or adjusted under 35 U.S.C. 154(b) by 35 days.

(21) Appl. No.: 12/537,837

(22) Filed: Aug. 7, 2009

(65) Prior Publication Data
US 2010/0040198 A1    Feb. 18, 2010

Related U.S. Application Data

(60) Provisional application No. 61/188,830, filed on Aug. 13, 2008, provisional application No. 61/178,249, filed on May 14, 2009.

(51) Int. Cl.
*A61N 5/10*    (2006.01)
(52) U.S. Cl. .......................................... 378/65; 378/145
(58) Field of Classification Search .................... 378/65, 378/145–159
See application file for complete search history.

(56) References Cited

U.S. PATENT DOCUMENTS

| | | | |
|---|---|---|---|
| 3,755,672 A | 8/1973 | Edholm et al. | |
| 5,014,290 A | 5/1991 | Moore et al. | |
| 5,825,845 A | 10/1998 | Blair et al. | |
| 6,080,992 A | 6/2000 | Nonaka et al. | |
| 6,381,304 B1 | 4/2002 | Shoenfeld et al. | |
| 6,980,871 B1 | 12/2005 | Sweat | |
| 7,154,107 B2 | 12/2006 | Yanagisawa et al. | |
| 7,456,415 B2 | 11/2008 | Yanagisawa et al. | |
| 2003/0086527 A1 | 5/2003 | Speiser et al. | |
| 2003/0102463 A1 | 6/2003 | Smith | |
| 2004/0228435 A1 | 11/2004 | Russell | |
| 2005/0058245 A1 | 3/2005 | Ein-Gal | |
| 2006/0015202 A1 | 1/2006 | Sweat | |
| 2006/0280288 A1 | 12/2006 | Speiser et al. | |
| 2007/0034812 A1 | 2/2007 | Ma et al. | |
| 2007/0040127 A1 | 2/2007 | Brahme et al. | |
| 2007/0053492 A1 | 3/2007 | Kidani et al. | |
| 2008/0027974 A1 | 1/2008 | Collins | |
| 2009/0096179 A1 | 4/2009 | Stark et al. | |
| 2009/0287333 A1 | 11/2009 | Sweat | |
| 2009/0287334 A1 | 11/2009 | Sweat | |
| 2009/0321632 A1 | 12/2009 | Grant et al. | |
| 2010/0230617 A1 | 9/2010 | Gall | |
| 2010/0303205 A1 | 12/2010 | Kapoor et al. | |

OTHER PUBLICATIONS

Compensator-intensity-modulated Radiotherapy—A Traditional Tool for Modern Application by Sha Chang, US Oncological Disease (2006) (pp. 81-84).
The .decimal Advantge: Solid IMRT on Demand, www.dotdecimal.com/products (2006).
U.S. Appl. No. 61/054,250, filed May 19, 2008, Sweat.

*Primary Examiner* — Courtney Thomas
(74) *Attorney, Agent, or Firm* — Jackson Walker, LLP

(57) ABSTRACT

An apparatus for engagement with a LINAC head of a LINAC machine, the LINAC machine generating radiation for intensity modulated radiation therapy of a cancer patient. The apparatus is a member incorporating separately a beam shaping material and a beam sculpting material. The member typically includes a tray and the tray is designed to fit into or adjacent the head of a LINAC machine. When radiation passes through the tray mounted member, it will be modulated and shaped to conform to the tumor of the cancer patient, which patient is radiated by the modified radiation beam.

22 Claims, 34 Drawing Sheets

Section View of the ISSU in the Accessory Adaptor of a LINAC

Figure 1 Model of a LINAC Prior Art

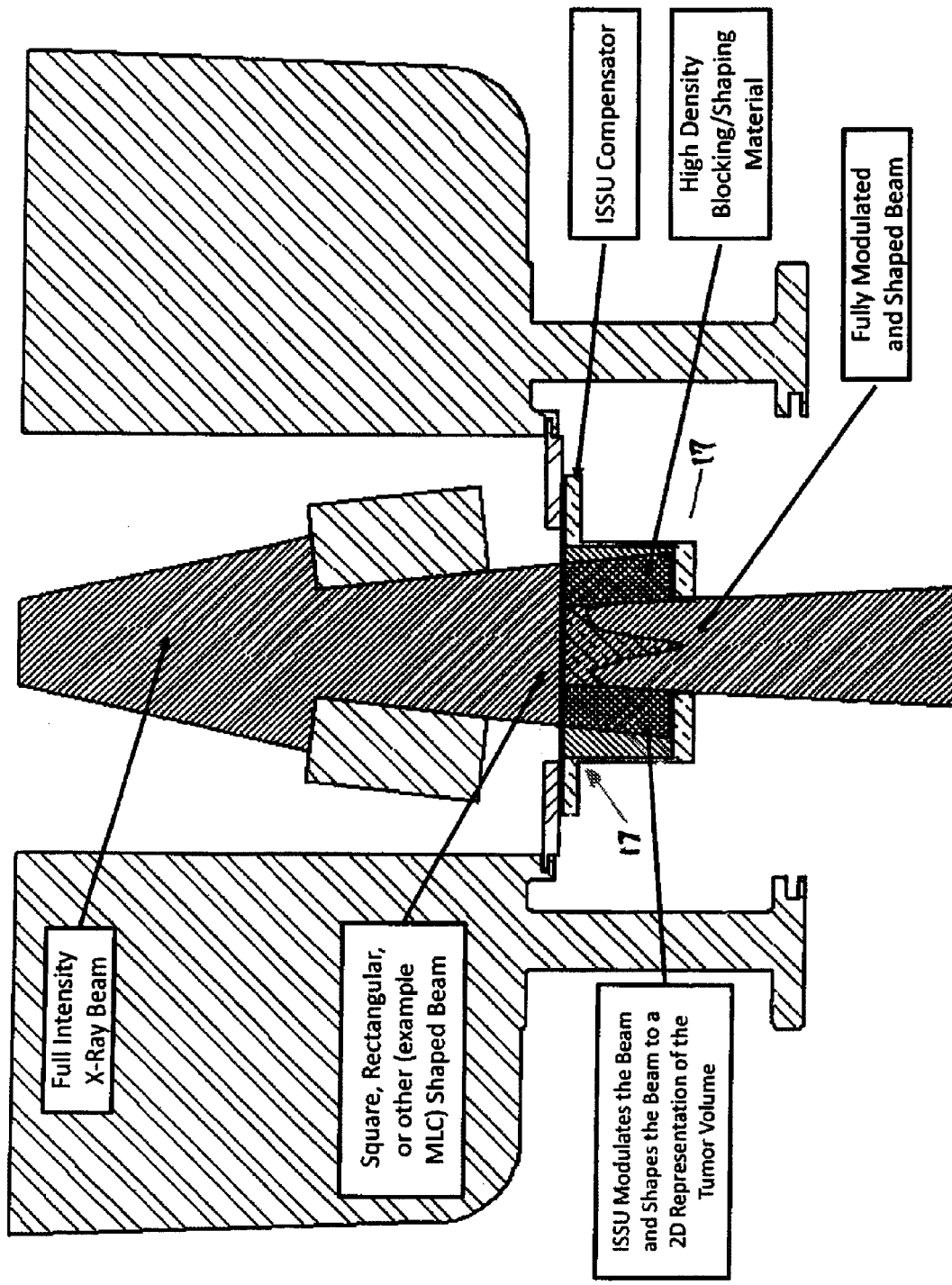
Figure 5 – Section View of the ISSU in the Accessory Adaptor of a LINAC

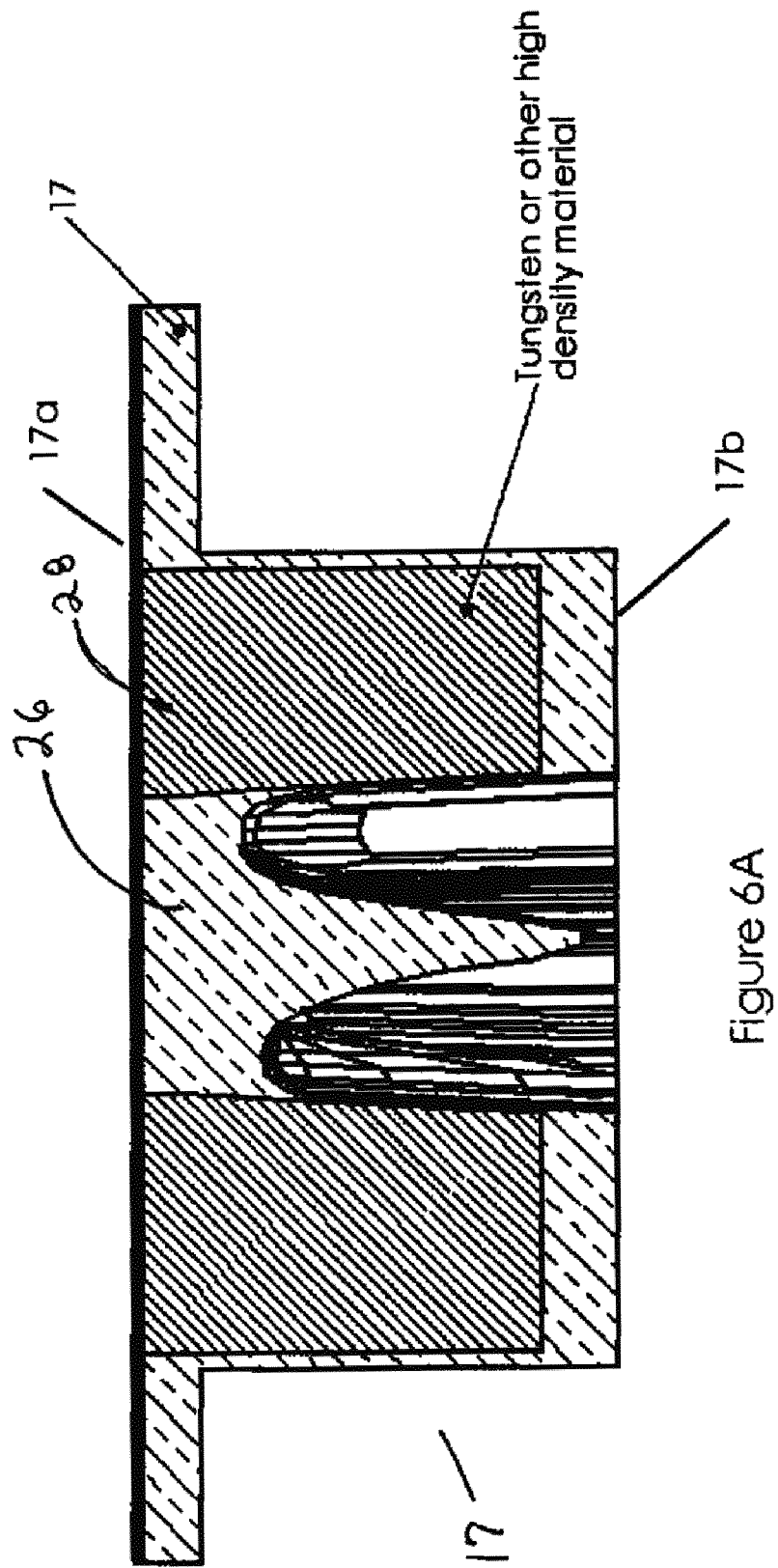

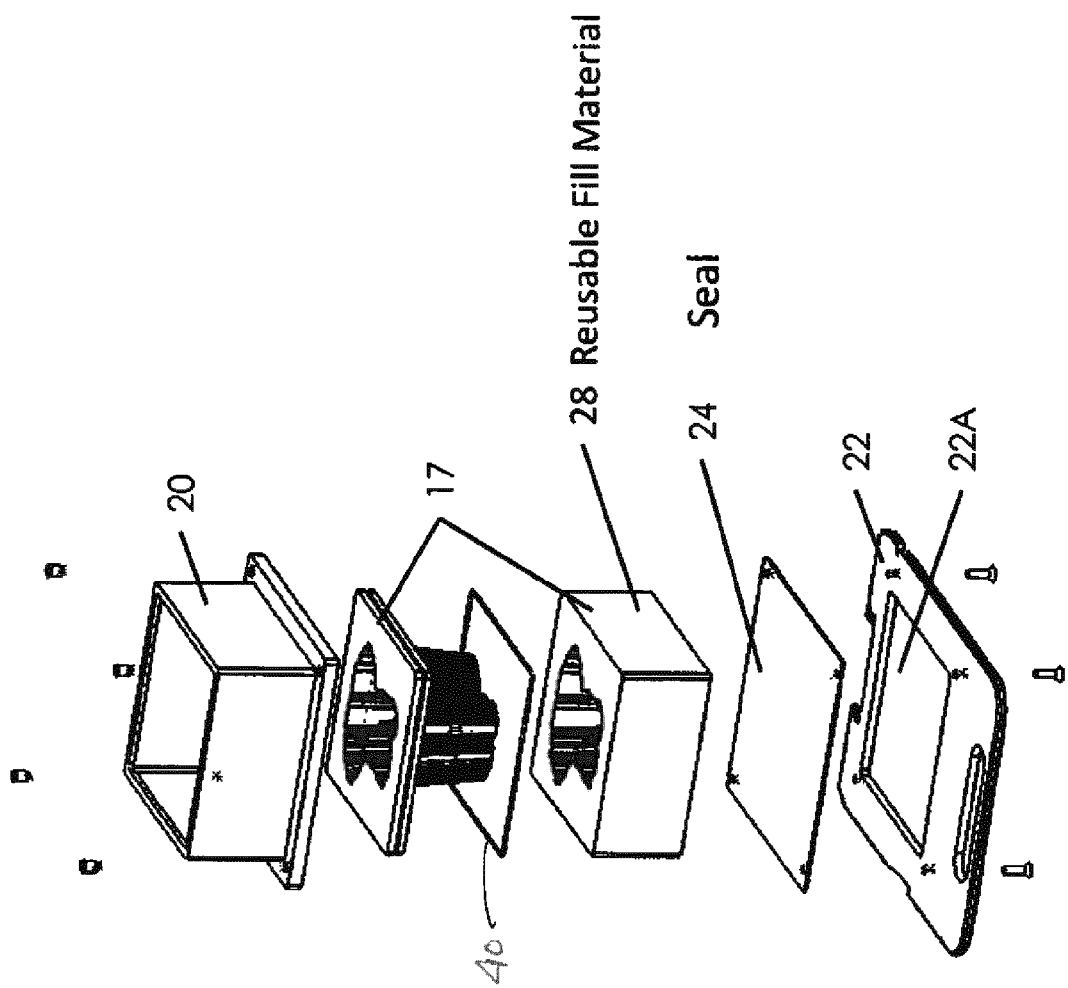

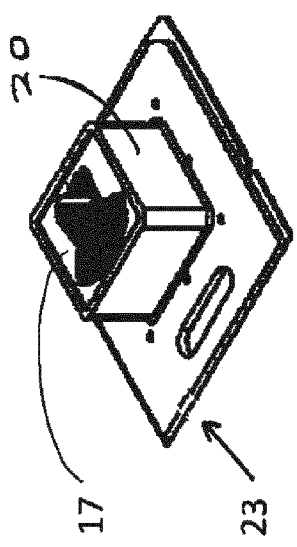
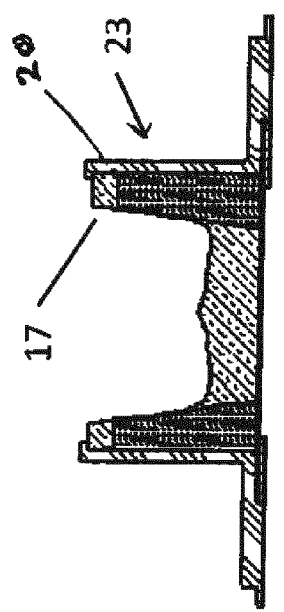
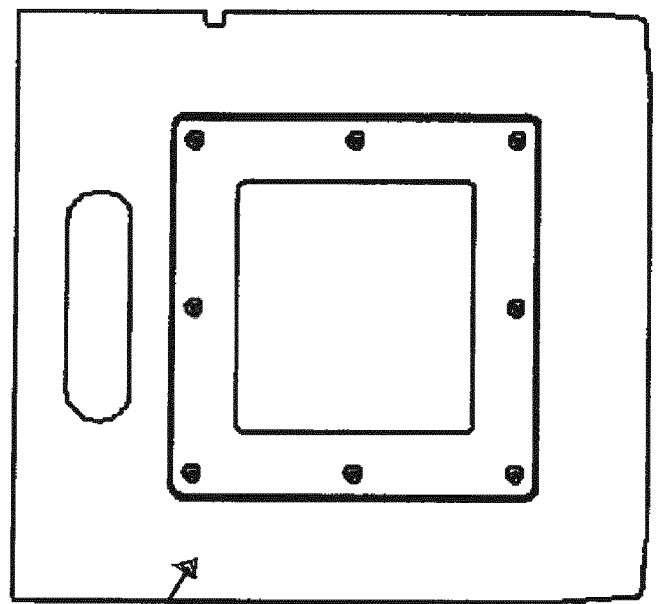
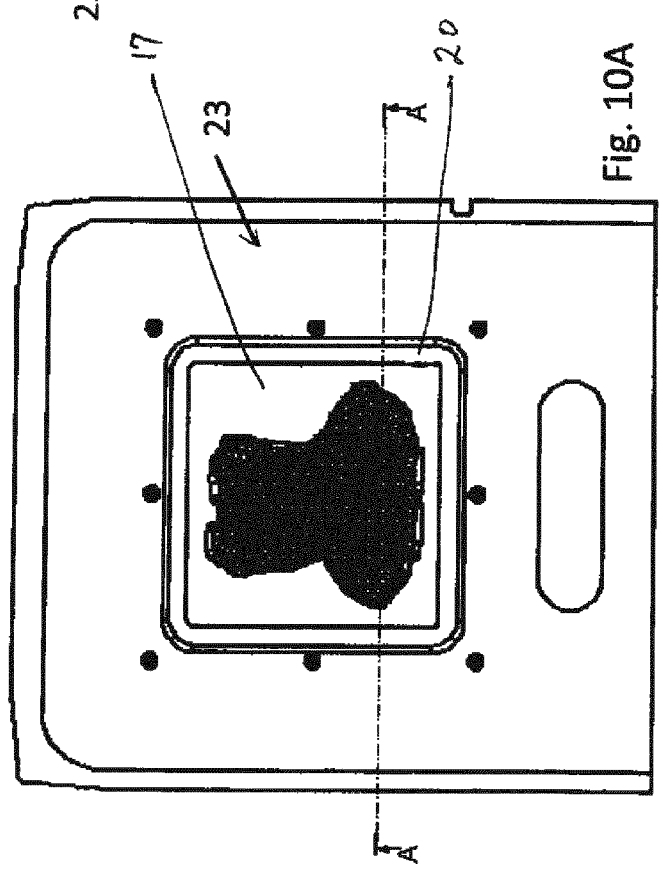

SECTION B-B

SECTION C-C

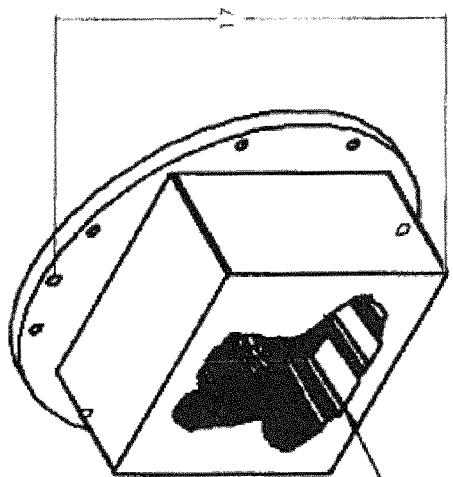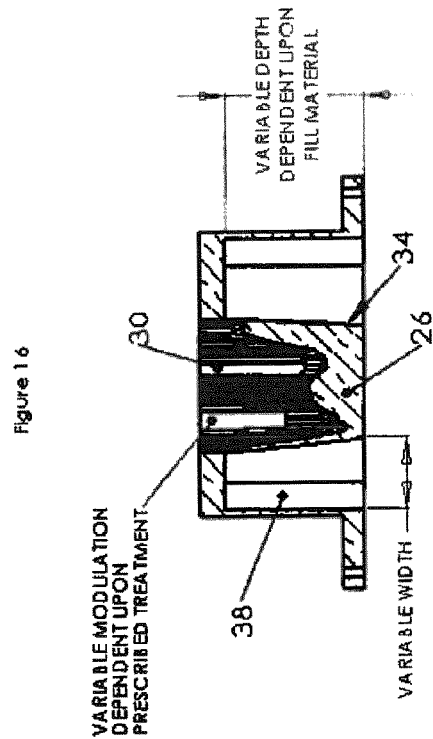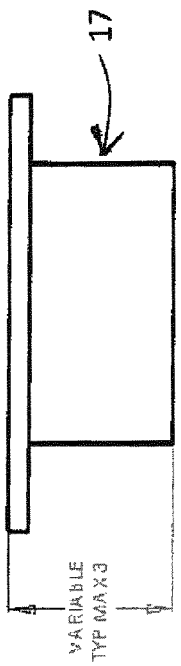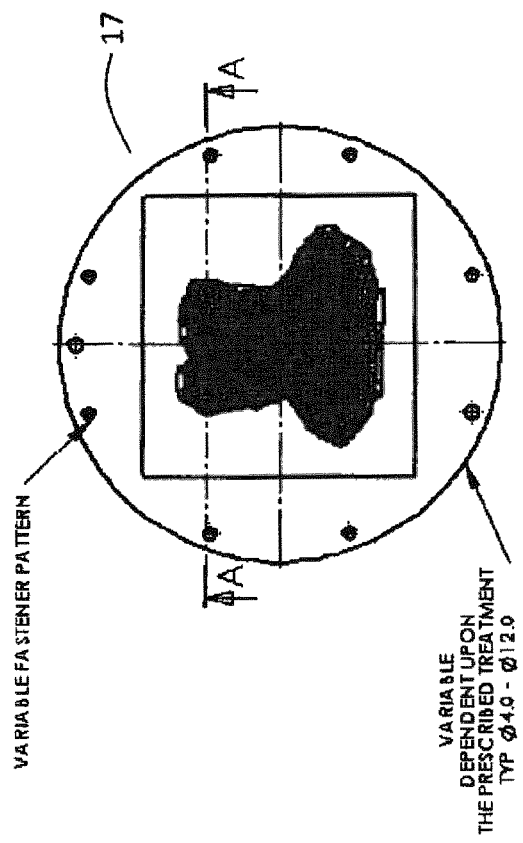

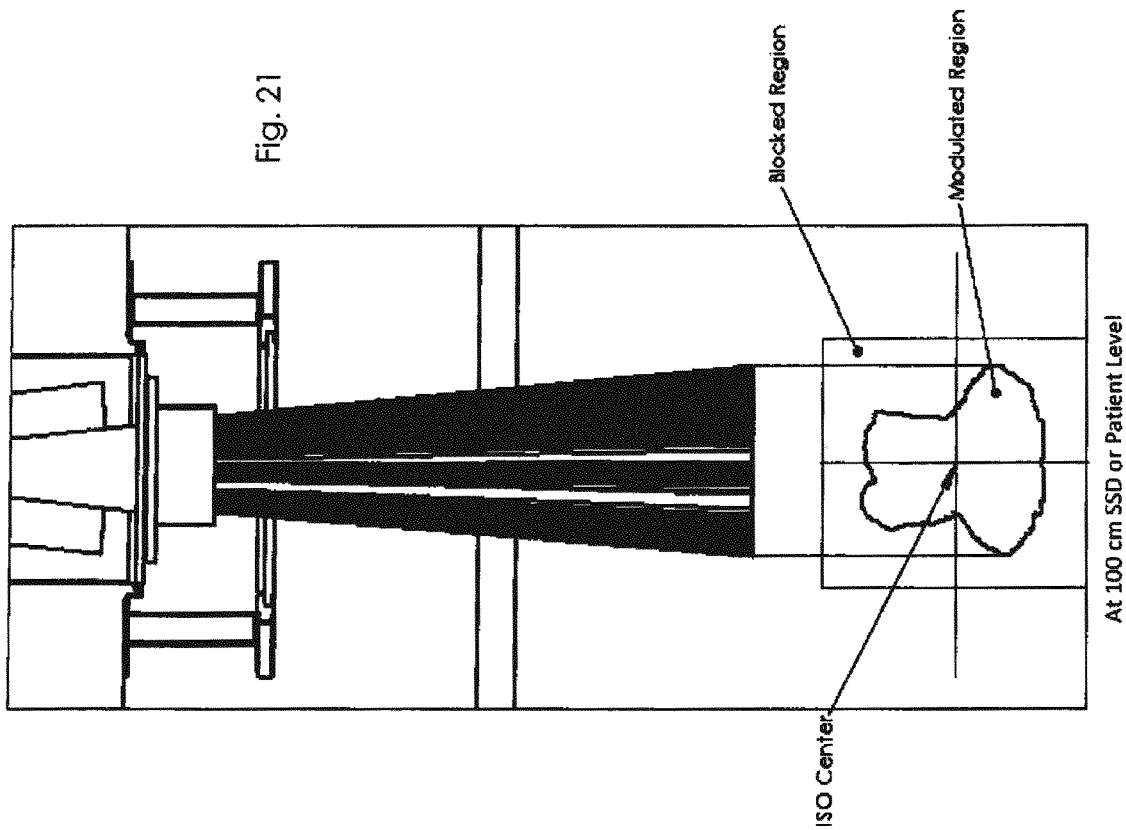

INTEGRATED SHAPING AND SCULPTING UNIT FOR USE WITH INTENSITY MODULATED RADIATION THERAPY (IMRT) TREATMENT

This application claims the benefit of, priority from, and incorporates by reference Application Ser. No. 61/188,830, filed Aug. 13, 2008, and Application Ser. No. 61/178,249, filed May 14, 2009.

FIELD OF THE INVENTION

Radiation oncology, including IMRT (Intensity Modulated Radiation Therapy) compensators and blocks.

BACKGROUND OF THE INVENTION

Radiation oncology is a branch of medicine that uses various types of radiation to treat and control cancer. Linear accelerators (LINACS) are used to deliver radiation to the patent for treatment. The radiation is typically in the form of X-rays and Gamma rays. X-rays and Gamma rays are high frequency ionizing light energy which has very short wavelengths. As the rays pass through matter they may lose energy or intensity by stripping the electrons off the atoms of the matter.

This ionizing of matter may destroy the DNA of cells. This is particularly effective against cancerous cells since, unlike healthy cells, they cannot easily repair damaged to their DNA. This results in the death of cancerous cells. Healthy tissue subjected to the same intensity of radiation as the cancerous cells can also die causing unwanted side effects.

To reduce the damage to healthy tissue, intensity modulated radiation therapy (IMRT) was developed with 3-D conformal radiation therapy. IMRT results in a "shaped" and "sculpted" beam which maximizes dose delivery to the cancerous tissue while minimizing dose delivery to the surrounding healthy tissue. By treating the tumor with controlled doses from multiple angles, total dose delivered to the cancerous tissue is equivalent to conventional treatment.

Compensator based IMRT uses a compensator mounted in the head of the LINAC to "sculpt" the beam and a block, if used, separately mounted below the compensator to "shape" the beam (see prior art FIG. 3).

The compensators and blocks are typically made out of high density material. The higher the density of the material, the more chance the radiation beam has to interact with the atoms of that material and lose energy or intensity as the beam passes through.

The beam emitted from the LINAC, before the compensator, is typically conical in shape. By using a block made out of a high density material with a cutout in the shape of the tumor in or around the middle of the block, the beam can be "shaped" by blocking the beam outside the tumor and allowing the full intensity of the beam in the two dimensional shape of the tumor to pass through. These blocks are typically molded out of a lead based alloy called Cerrobend® and are typically 2 to 3 inches thick when used with compensators.

The compensator and the block (if used) are typically aligned with the central axis of the radiation beam and the compensator lines up with the cutout in the block and modulates the intensity of the beam. The compensator is typically milled out of brass, aluminum, bronze, tungsten, Cerrobend®, other suitable material depending on the initial intensity of the beam and "sculpts" the beam by having little material thickness where the beam has line of sight to the tumor and more material where the beam lines up with healthy tissue and critical structures of the body (see prior art FIGS. 4 and 4A).

Each patient is treated typically with 3 to 11 differently shaped compensators and typically their corresponding blocks. Even though this style of treatment is very effective for the patient, there are several drawbacks for the centers administering the care.

1. The biggest drawback for the center is handling and working with a hazardous material such as the Cerrobend. Special rooms and ventilation systems are required to protect the health of the employees and to prevent any lead dust from escaping the block room and contaminating the rest of the hospital.
2. The center must have a trained and experienced block maker on staff.
3. Special trays are required to mount the blocks on. These trays are typically made out of Acrylic and degrade with time due to radiation exposure. This causes the material to become brittle and dangerous for use around patients.
4. Each block must be matched up with the correct compensator for treatment or the patient may be harmed. This is made more difficult due to the fact that for each angle the patient is treated from, a different compensator and block is required. These are changed out "on the fly" during each treatment.
5. The block must align correctly with the rest of the system or the patient may be mistreated. This depends upon the tolerances of the adaptor, tolerances of the block tray, and the competency of the block maker.

Some centers have opted to get rid of the separate blocks by, typically, doing one of two things.

A. The center uses an extremely high density material, such as cast Cerrobend or tungsten powder, to create a combination block and compensator. These devices successfully act as beam shapers to substantially reduce dose to surrounding healthy tissue, but the relatively high density of the material magnifies any error in the modulation of the beam due to manufacturing tolerances, voids and shrinkage which is inherent to the casting process, and shifting of the powder.

B. Due to the drawbacks associated with using high density material to create a combination block and compensator, many centers that have opted to eliminate separate beam shaping blocks during treatment have selected materials commonly used for compensators which have good beam modulating or "sculpting" characteristics, typically brass and aluminum. These materials are less dense than materials used specifically for beam blocking and therefore do not magnify errors due to manufacturing tolerances as much as the higher density materials do. This results in a more accurate dose being delivered to the tumor. Unfortunately, the lower density of the material allows a high dose to be delivered to the surrounding tissue than would normally have occurred if separate, high density blocks were used.

A radiation oncologist and physicist prepare a treatment plan, specifically for the specific patient. The plan includes restraints for radiation exposure for critical structure as well as restraints or a prescription for radiation of the tumor area. From these parameters, a specific treatment plan for the patient is prepared. These parameters are sent to a manufacturer for preparing, in ways known in the art, the compensator and block, if used, that will provide the plan parameters for the LINAC machine used.

Radiation is initially projected by the LINAC head in a multiplicity of pencil beams directed generally towards the tumor target area (such as a cancerous organ) on a patient. The beam, after initial projection, is subsequently modified by the conventional processes of shaping and sculpting. Generally, shaping is the process of defining an external boundary or a through profile that will cover the profile (projected outline) of a target tumor as projected downstream from the various shaping mechanisms. The shaping mechanisms are typically jaws (LJ) upstream of the conventional compensator and a conventional block, CB, for example, comprising Cerrobend®, separate from and mounted downstream of a conventional compensator.

IMRT typically modulates (sculpts) the intensity of the radiation that falls within the through profile by means known in the art, typically, machining a compensator into an inverse contour represented by the tissue variation dictating by target dosage.

As illustrated in FIGS. 3, 4 and 4A, the material compositions of the conventional compensator and Cerrobend block are usually different (typically, the block has a material of greater density), but they are also shaped differently, dictated by their differing functions. Ideally, if used, the block has a profile shaping function and the compensator acts to modify or sculpt, as by modulation, the intensity of the radiation passing through the compensator profile. Moreover, while gross beam shaping or blocking is provided upstream of the conventional compensator by jaws LJ, the shaping is refined by a conventional block (if used) mounted downstream of a separate conventional compensator as illustrated in FIG. 3.

Typically, conventional compensators mount on a conventional compensator tray (CCT) as by conventional fasteners engaging a flange on the conventional compensator and the tray. Conventional compensator tray (CCT) has a pair of spaced apart ridges for engagement with upper slots (US) in the accessory adapter (AA) of a typical LINAC machine.

Similarly, a conventional block (CB) may be mounted by fasteners or in other ways known in the trade to a conventional block tray (CBT) which, as with the conventional compensator tray (CCT), has ridges spaced apart for joining lower slots (LS) on an accessory adaptor (AA) of the typical LINAC machine for engagement with a wedge tray slot.

Thus, typically the conventional compensator and conventional block are handled separately and are positioned vis-à-vis one to the other through careful placement on trays and careful placement of the trays in the accessory adapter (AA) of the LINAC machine (LM).

SUMMARY OF THE INVENTION

An apparatus for engagement with a LINAC head of a LINAC machine, the head having an engagement member for IMRT of a cancer patient; a beam modification member incorporating separately both a beam shaping material and a beam sculpting material, the member for placement in the LINAC head for modification of the IMRT beam.

A method of treating a cancer patient with IMRT; irradiation of a tumor in a cancer patient wherein the radiation is modified by engagement of a beam modification member with the LINAC head, the member incorporating separately both a beam shaping material and a beam sculpting material, wherein the member includes walls defining a shaping cavity, wherein at least some of the walls defining a shaping cavity are comprised of the beam sculpting material, and wherein at least some of the walls of the cavity substantially define a shaping profile.

The shaping cavity may contain the beam shaping material and the beam shaping material may be a fluid. The fluid may be one of the following: tungsten, a tungsten binder mix, a ferrous and resin mix, and Cerrobend.

The shaping material may be one of the following: tungsten (solid, powder, shot, tungsten shot and tungsten powder mixture, liquid or in slurry form), lead and/or Cerrobend (solid, powder, powder/solid shot mixture or liquid form or any other suitable dense material (solid, solid/powder, shot/powder), wherein the shaping material may have a density of between about 2.5 and about 20 grams/cubic centimeter.

A tray may be provided and the beam modification member may be engaged to the tray. The tray may be adapted to engage the head of a LINAC.

The beam modification member may include a flange. The flange may be made at least partially from the sculpting material. The flange may be adapted to engage the tray. The flange may be made at least partially from the sculpting material.

A shroud may be provided, the shroud adapted to engage the beam modification member and the tray. The tray or the shroud is typically made from acrylic or polycarbonate.

A seal plate may be adapted to engage the beam modification member to seal a shaping cavity. The sculpting material may be solid and include walls defining a sculpting profile and the shaping material may be solid and contain walls defining a shaping profile. The beam modification member may be substantially cylindrical, substantially rectangular (including cubic). An integrated shroud/tray may be provided for engagement of the beam modification member to the LINAC head.

The purpose of the integrated design is to eliminate the need for separate blocks by providing a product which can both modulate or "sculpt" the beam and effectively block the transmission of radiation outside the volume of the tumor as effectively as using a separate compensator and block fabricated from different materials.

In one aspect of this invention, this will be accomplished by taking a conventional compensator shape or profile and milling a pocket in the compensator material outside the modulated area (see FIGS. 5 and 6). This pocket will follow the same contour as the conventional block. The pocket can also be milled more accurately to the shape of the tumor than the block can be cast or cut with a hot wire. Once milled, the pocket can then be filled with a high density material such as tungsten, Cerrobend, etc. as set forth more fully below.

Tungsten (19.3 g/cm$^3$) is one high density fill material. Another is a tungsten and ferrous binder mix; it is twice as dense as Cerrobend (9.38 g/cm$^3$) and almost completely inert. The pocket can be filled with solids, powder, or a combination of the two. Tungsten powder can also be mixed with a resin for injection molding or casting. These forms typically result in an apparent density which is slightly higher than pure lead (11.34 g/cm$^3$). The tungsten/resin mix ratio (or for any shaping material) can be altered to give a density range of 8 to 19.3 gm/cm$^3$. Granulated tungsten, typically sieve 20-80, may be used, alone or with tungsten powder, typically sieve 100-500. Density of a mix may be adjusted to any pre-selected appropriate range. A mix would include a suitable binder and a suitable shaping material, mixed in a ratio to give a suitable density.

This product has several advantages for both the patient and the center.

1. The center no longer has to deal with a hazardous material.
2. The center no longer needs a special room and specialized personnel.

3. The chance of mistreating a patient due to mismatching compensators to their blocks or due to sloppy workmanship is eliminated.
4. Patient treatment time is reduced due to the reduction of hardware and setup time.
5. The center does not have to compromise between protecting surrounding tissue or delivering accurate dose to the tumor if they wish to eliminate separate blocks.

BRIEF DESCRIPTION OF THE DRAWINGS

FIGS. 5, 5A, 5B, and 5C illustrate Applicants' new integrated compensator/block unit, its relationship to a LINAC head and how it modifies a LINAC beam.

FIGS. 6A and 6B illustrate a preferred embodiment of Applicants' integrated compensator/block unit.

FIGS. 8, 9 and 10 provide additional illustrations of a shrouded embodiment of an ISASU.

FIGS. 10A-10E illustrate an integrated shroud/tray unit 23.

FIGS. 16, 16A, 16B, and 16C illustrate the general construction of an embodiment of an ISASU.

FIG. 21 illustrates a method of making Applicants' novel ISASU 17.

DETAILED DESCRIPTION OF THE PREFERRED EMBODIMENTS

Figure 1:
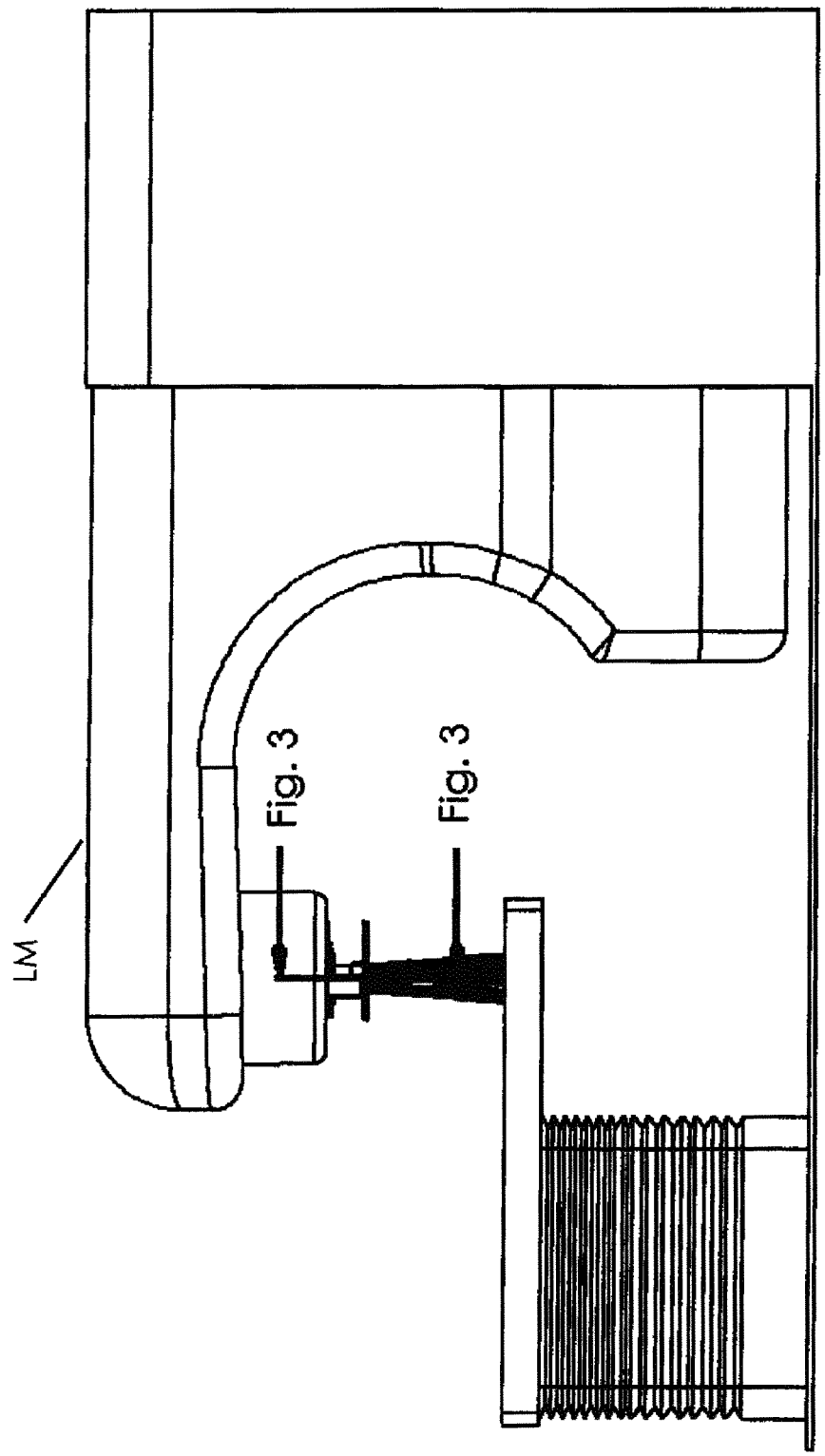
FIG. 1 illustrates a typical prior art LINAC machine.
Figure 2:
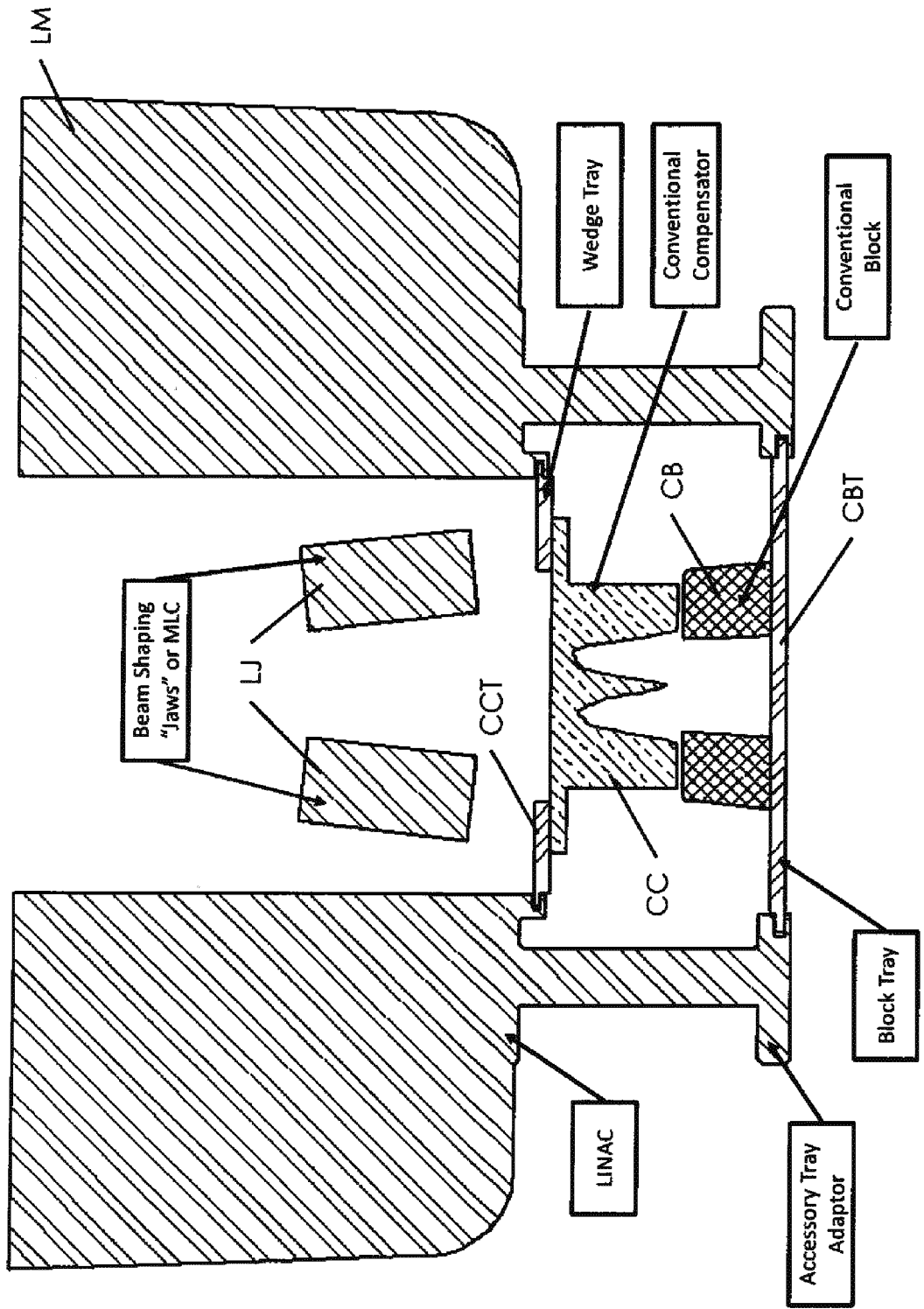
FIGS. 2, 3, 4, and 4A illustrate conventional prior art compensators, conventional blocks and their relationship to an accessory adaptor and a modified beam from the LINAC head.

FIGS. 1 and 2 illustrate a typical prior art LINAC machine (LM). A LINAC machine will provide multiple "pencil" beams of radiation, predominantly gamma rays and x-rays in ways known in the art. As seen in FIGS. 2, 3, 4, and 4A, a prior art LINAC machine (LM) uses jaws (LJ), typically four, to provide an initial beam blocking upstream of a conventional compensator (CC) and a conventional block (CB) (if used) located downstream of the beam source, and separately attached on an accessories adapter (AA).

Figure 5A:
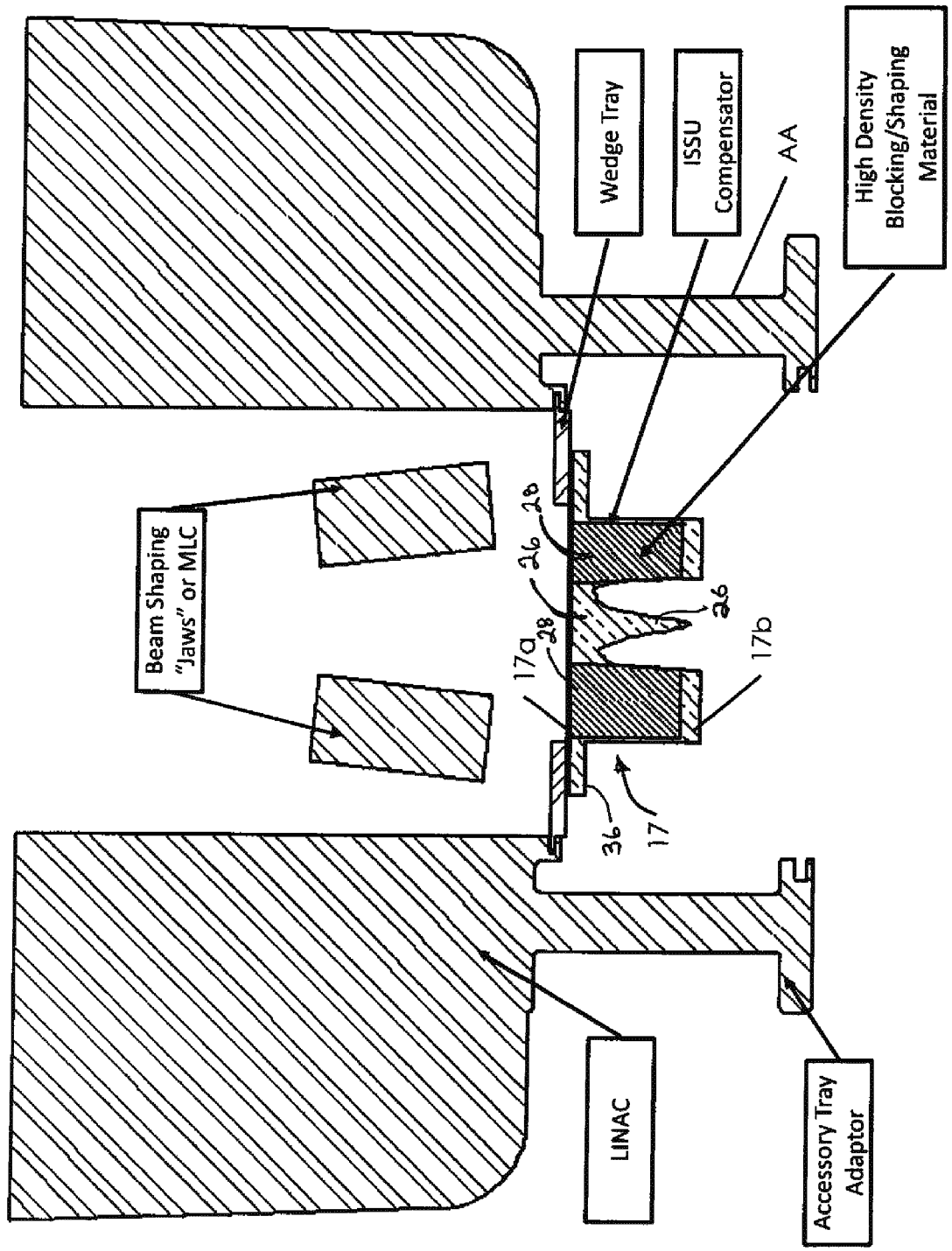
Figure 5B:
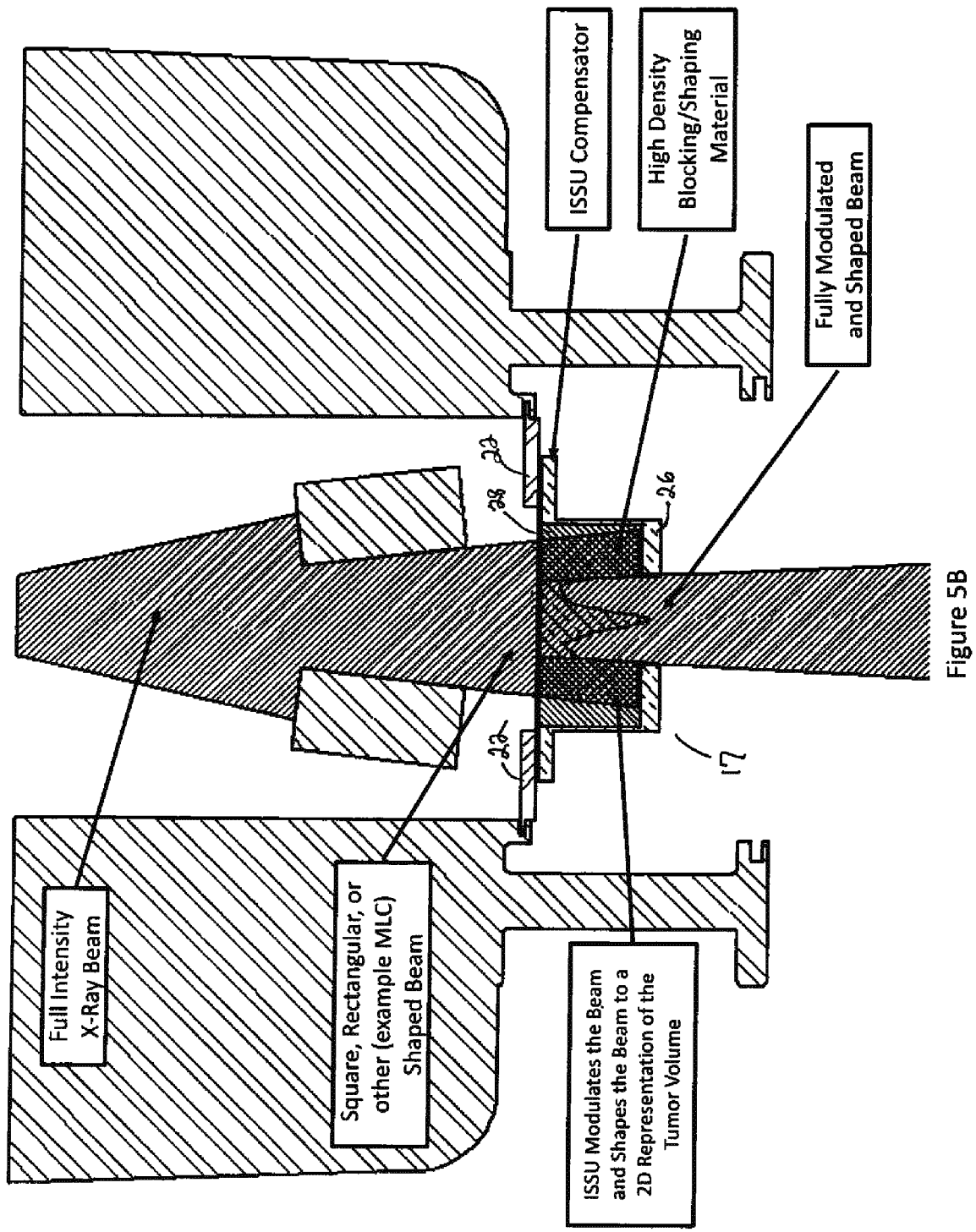
Figure 5C:
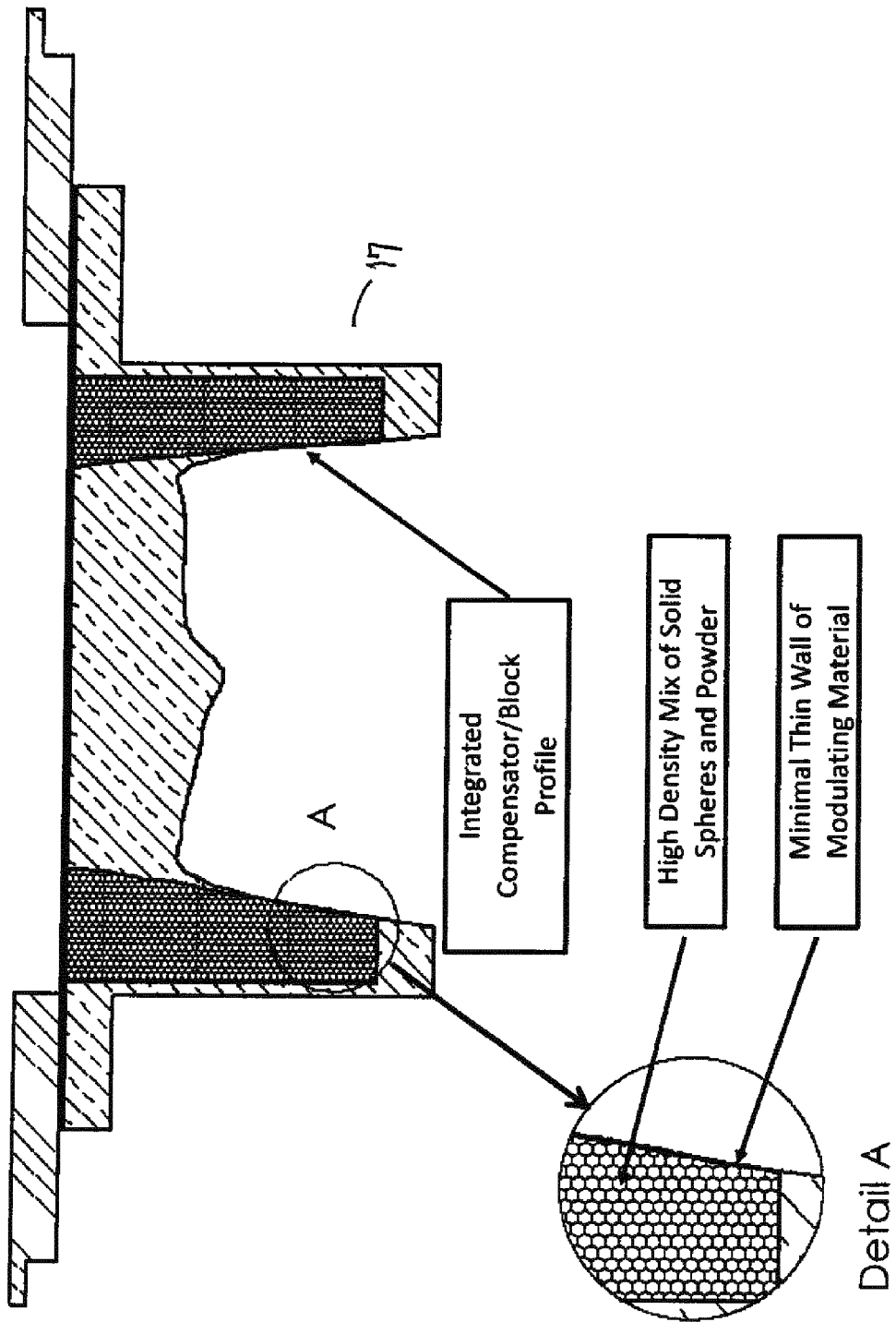
Figure 6B:
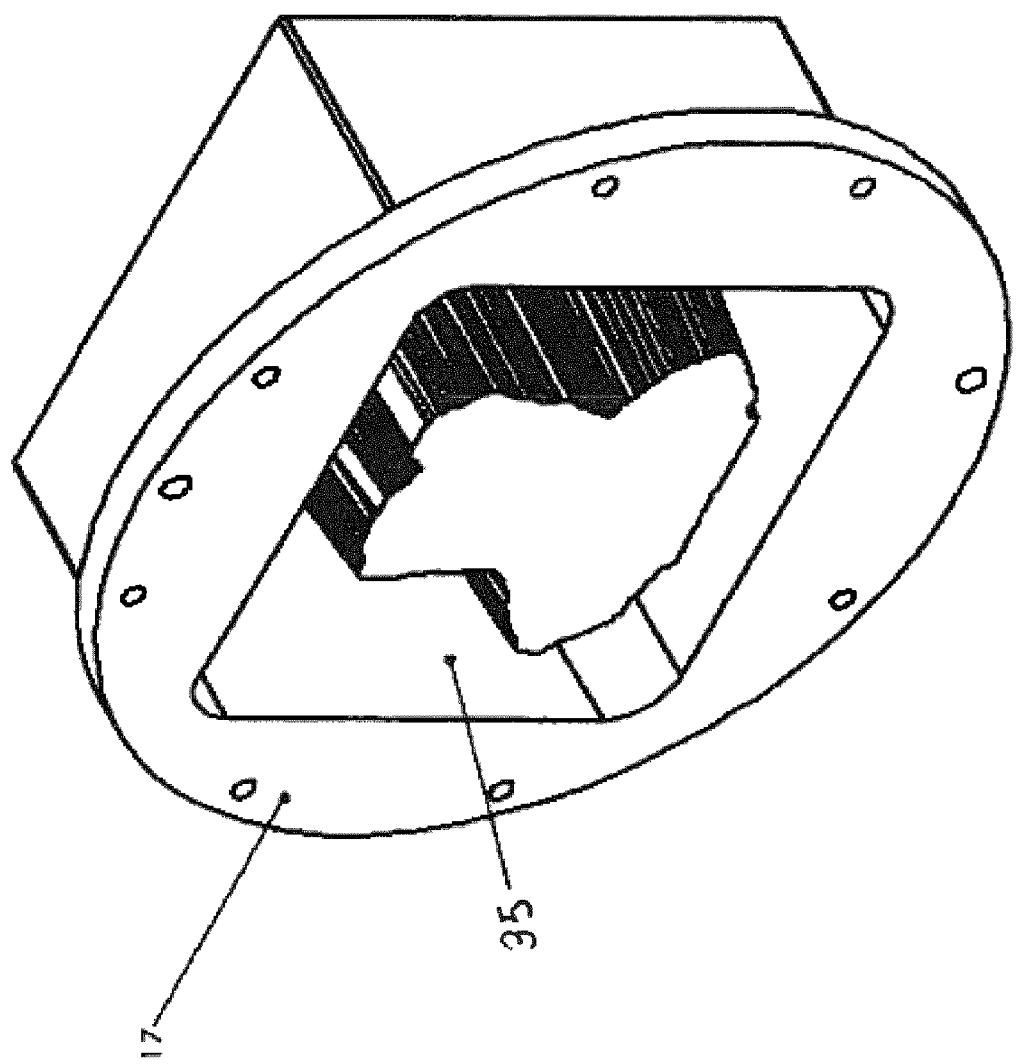

FIGS. 5, 5A, 5B, 5C, 6A, and 6B illustrate the integrated sculpting and shaping unit or beam modification member (ISASU) 17 in one preferred embodiment. In this embodiment, the ISASU 17 has outer boundaries or surfaces substantially comprising the sculpting material 26 and the shaping material 28 is in a shaping cavity 35 (see FIG. 6B) or cavities formed substantially within the sculpting material. A flange 36 is provided, typically made from sculpting material for engagement with a tray 22. ISASU 17 has a near end 17a and a removed end 17b, the removed end may be directed towards the patient as seen in FIG. 5A, or the tray 22 may be rotated 180 degrees from the position as seen in FIG. 5A, so that the removed end is away from the patient (not shown).

Figure 3:
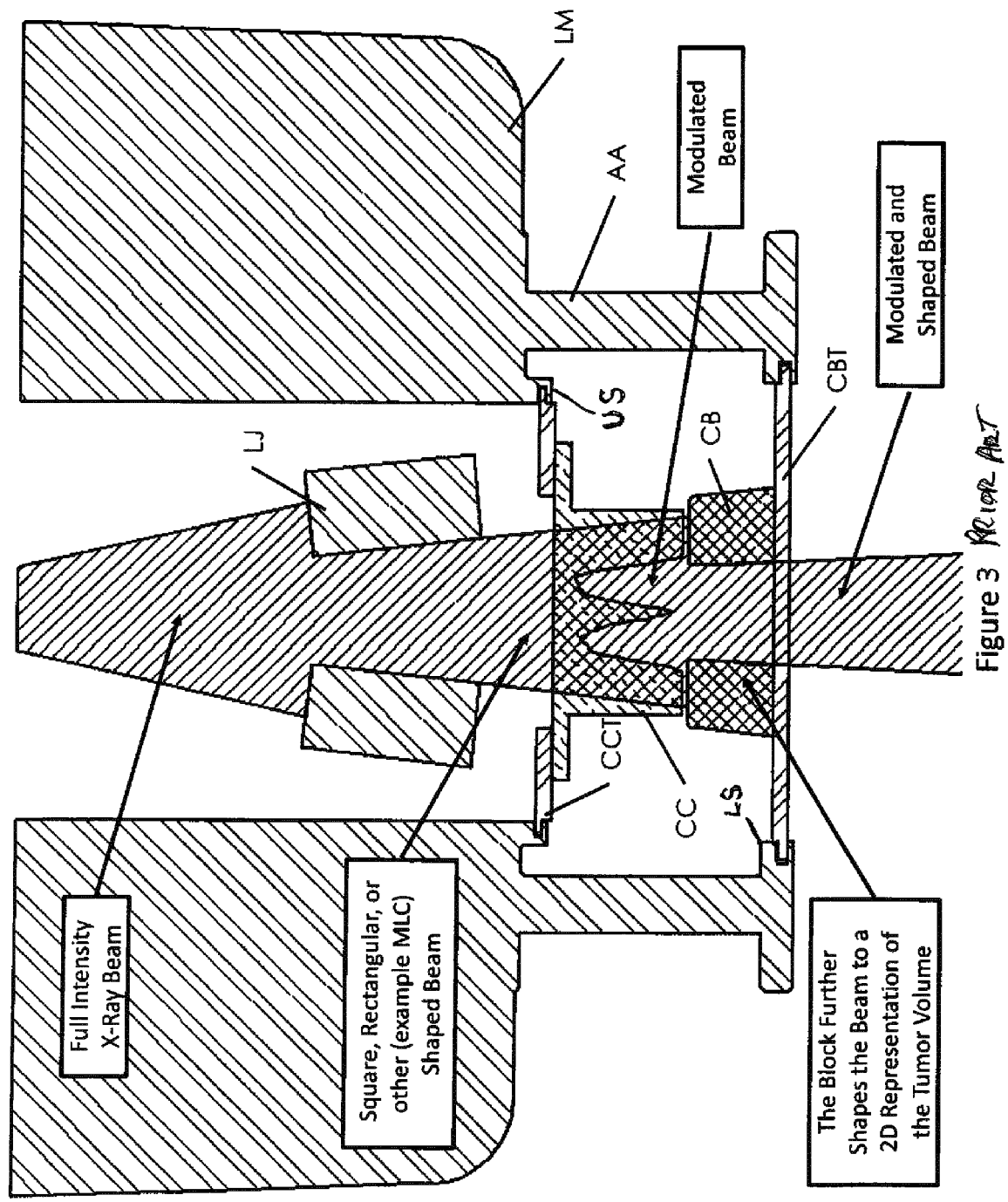
Figure 4A:
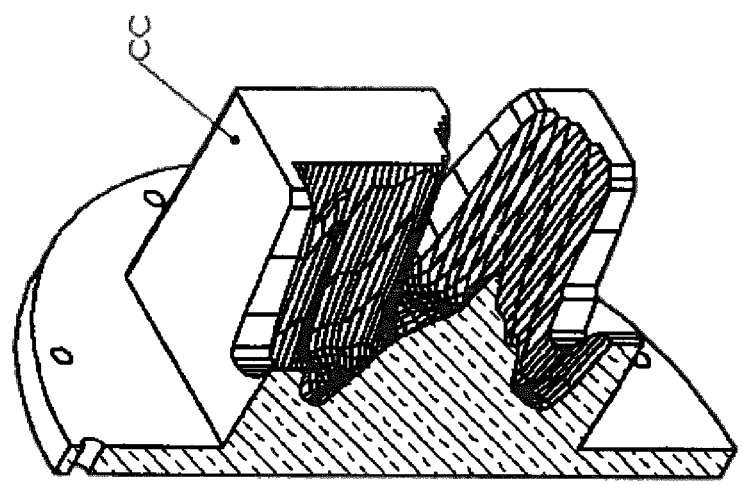
Figure 4:
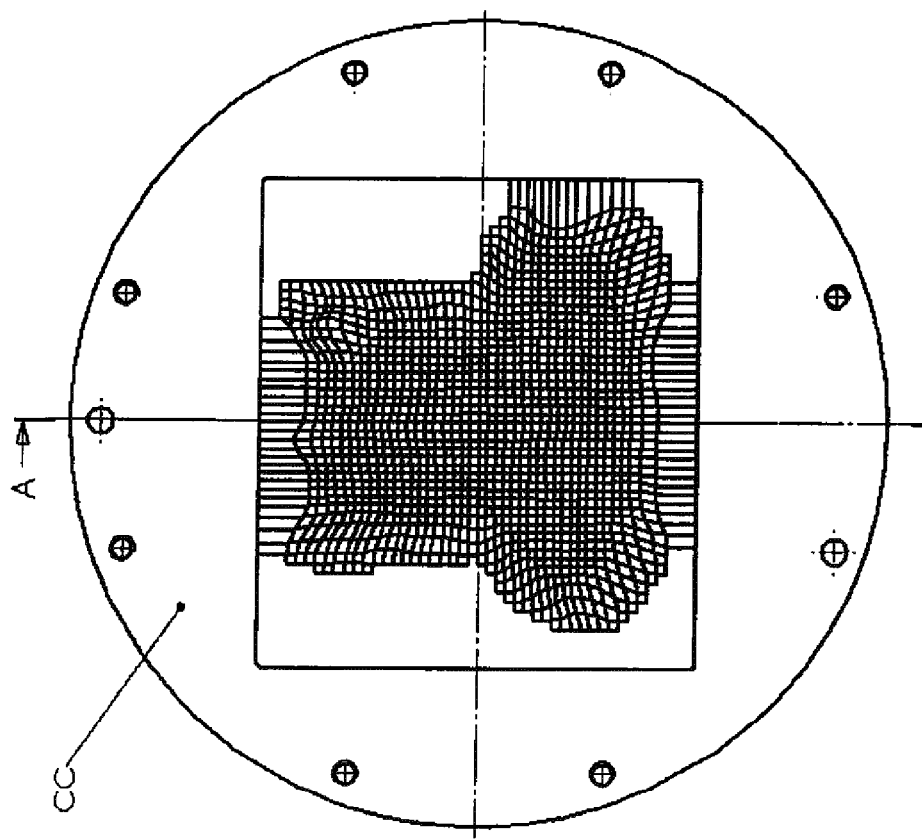

Generally, as set forth above, an ISASU 17 will integrate into a unit at least two materials—discrete separate sculpting material(s) that functions to modulate radiation and discrete shaping material(s) whose function is to control a through profile to shape the beam such that the at least two materials are capable of being transported as a unit and mounted or positioned on a LINAC as a unit or member, with the two portions fixed positionally and spaced one with respect to the other rather than separately transported and mounted as seen in prior art FIGS. 3, 4 and 4A. In a preferred embodiment, walls defining a shaping function (modulation) and a shaping material, and walls defining a sculpting function and sculpting material, will be in a single unit. ISASU typically may include, though it is not necessary, some form of mounting apparatus for mounting to an adaptor or tray, which in turn adapts the ISASU for removable attachment to the LINAC.

Figure 7:
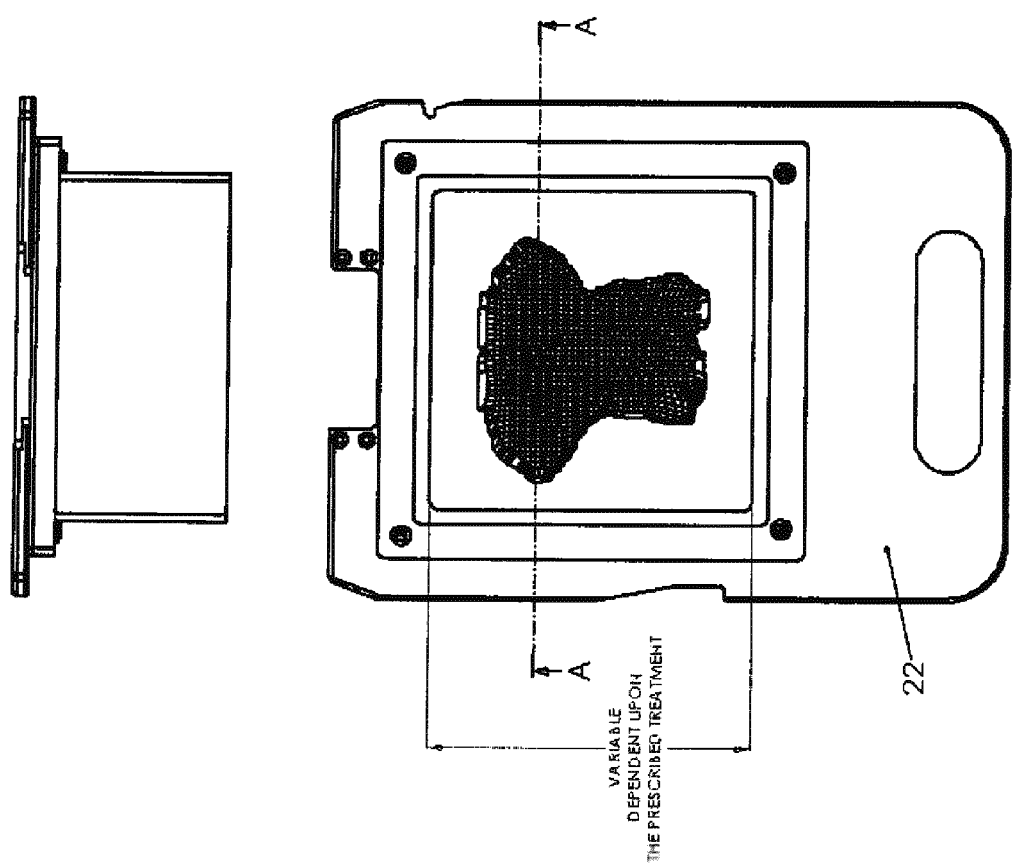
FIGS. 7, 7A, and 7B illustrate a shrouded ISASU 17.
Figure 7A:
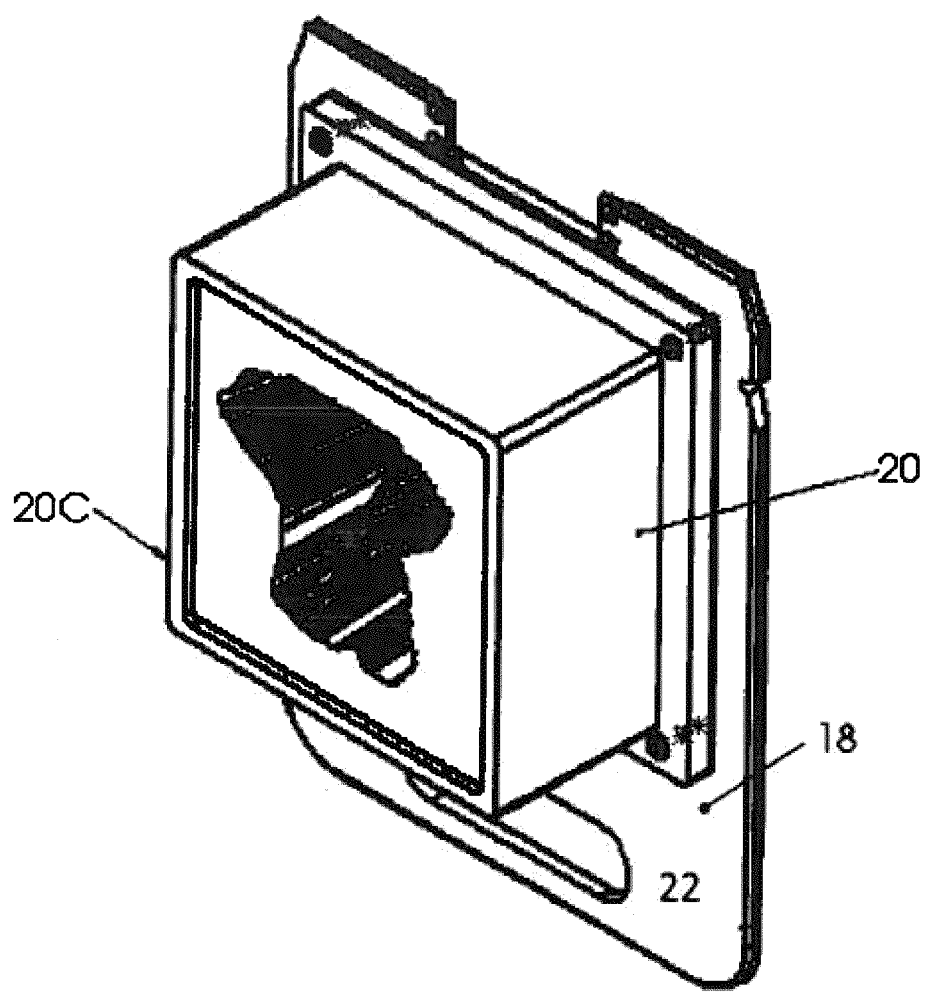
Figure 7B:
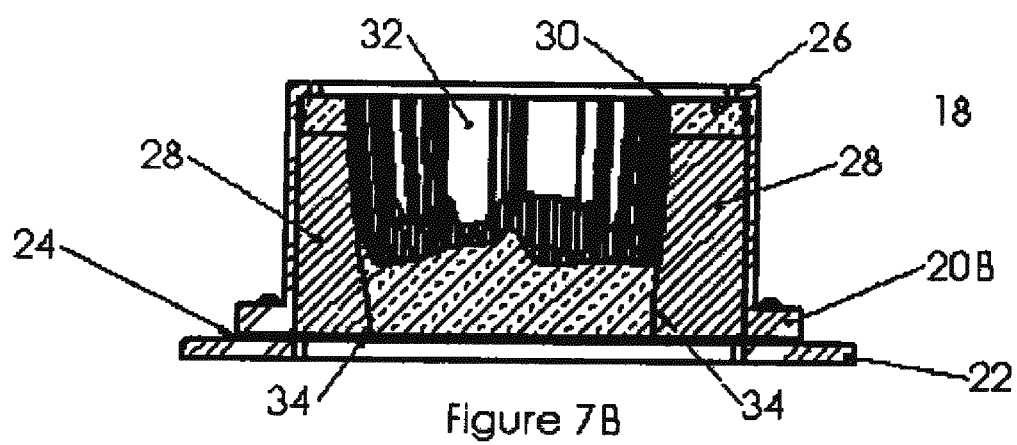

Generally, the two materials of the ISASU 17 include a substantially sculpting portion material 26 and a substantially shaping portion material 28 (See FIG. 7B). Examples of typical sculpting materials include brass, or aluminum, tungsten, composites, alloys, or any other suitable material. Examples of typical shaping portion materials or shaping materials include tungsten (solid, powder, shot, tungsten shot and tungsten powder mixture, liquid or in slurry form), as well as the following materials alone or in combination: lead and/or Cerrobend, again, in solid, powder, powder/solid shot mixture or liquid form or any other suitable dense material (again as solid, solid/powder, shot/powder, etc.), including, for example, depleted uranium (density about 19 grams/cc). It is noted that, while the sculpting portion material is typically solid, the shaping portion material may be solid or powder, a powder/shot mixture, liquid, gel, a two or three phrase system, a flowable or a fluid material or the like. A fluid is any material or substance that changes shape or direction uniformly in response to an external force imposed upon it. The term applies not only to liquids, but to gases and finely divided solids.

Figure 8:
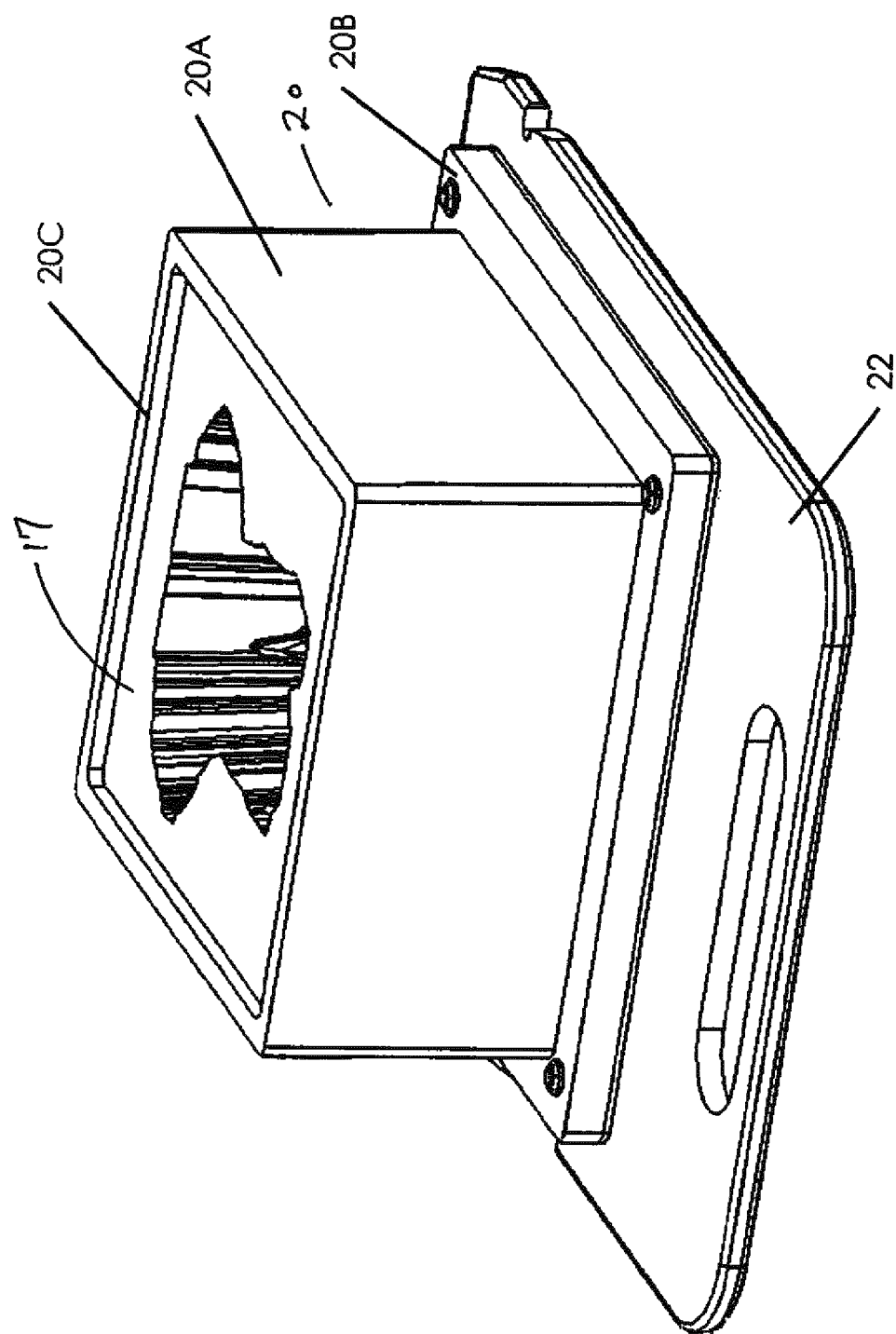

It is further seen that ISASU 17, in FIGS. 7, 7A, 7B, 8, 9, and 10, may be mounted to a mounting and locating tray 22, dimensioned as prior art trays to the extent that they are adapted to engage a typical LINAC machine. A tray 22 is a member that engages the head of the LINAC, directly or indirectly, so the ISASU 17 is in, on, near or adjacent the head. It may be made from acrylic, polycarbonate, plastic, PVC or any other suitable material. Moreover, engagement of ISASU 17 to tray 22 may provide a combined ISASU/tray unit 18 (see FIG. 9). The combination of ISASU 17, when ISASU typically takes a rectangular shape as seen in FIG. 8, may be accomplished with the use of a shroud 20, typically having a shroud body 20A, a shroud flange 20B, and a lip 20C. That is to say, the use of a shroud with an ISASU 17 allows the joinder of the ISASU 17 to the tray 22. In a preferred alternative embodiment, the ISASU 17 includes a flange 36 (see FIGS. 11, 11A, 11B and 12) and, optionally, a seal plate 24/25 is set forth more fully below.

Turning back to FIGS. 7, 7A, 7B, 8, 9, and 10, it is seen that a seal plate (full) 24 may be provided between a shroud 20 and the tray 22, which shroud and full seal plate is especially useful when shaping material 28 is in the nature of a powder, fluid, slurry or liquid. A seal may be eliminated when a full tray (that is, without cutout area) is used. In conjunction with walls of shroud body 20A and optionally a reusable gasket seal 40 for example an O-ring seal (see FIG. 9), the structure will achieve a sealing function preventing the escape of a liquid, slurry or powder. On the other hand, if shaping portion 28 is a solid material, it may be poured molten into shaping portion cavity 38, which includes shaping portion walls 34

(see FIGS. 16, 16A-16C). Sculpting portion cavity 32 is defined by milled walls 30 and is prepared by methods known in the art.

As set forth above, mounting tray 22 is dimensioned, especially in its external perimeter, to mirror conventional compensator tray (CCT) as set forth above so as to engage conventional wedge slots. Further, mounting tray 22 may be dimensioned to engage accessory adapter in either the upper or lower tray slot. However, tray 22 may be adapted to receive shrouds and, further, the shrouds may come in a multiplicity of body 20A sizes, standardized for a range of external dimension standardized ISASU 17. For example, the ISASU 17 may be rectangular with the following general dimensions: L-W-H, 3×3×3 inches, another may be 4×4×3 inches. However, for standardization, lip 20D would have the same bolt hole pattern regardless of the dimension, here four at the four corners of the flange. In this manner, shrouds 20 would be reusable and the standardized ISASU 17 would fit within the pre-selected one of the standardized shroud body sizes, but whatever size shroud/ISASU combination was chosen, it would fit to a standardized one-size-fits-all tray 22 with common bolt pattern for different shrouds. However, standardized shroud/units may be used with different sized trays.

Figure 9:
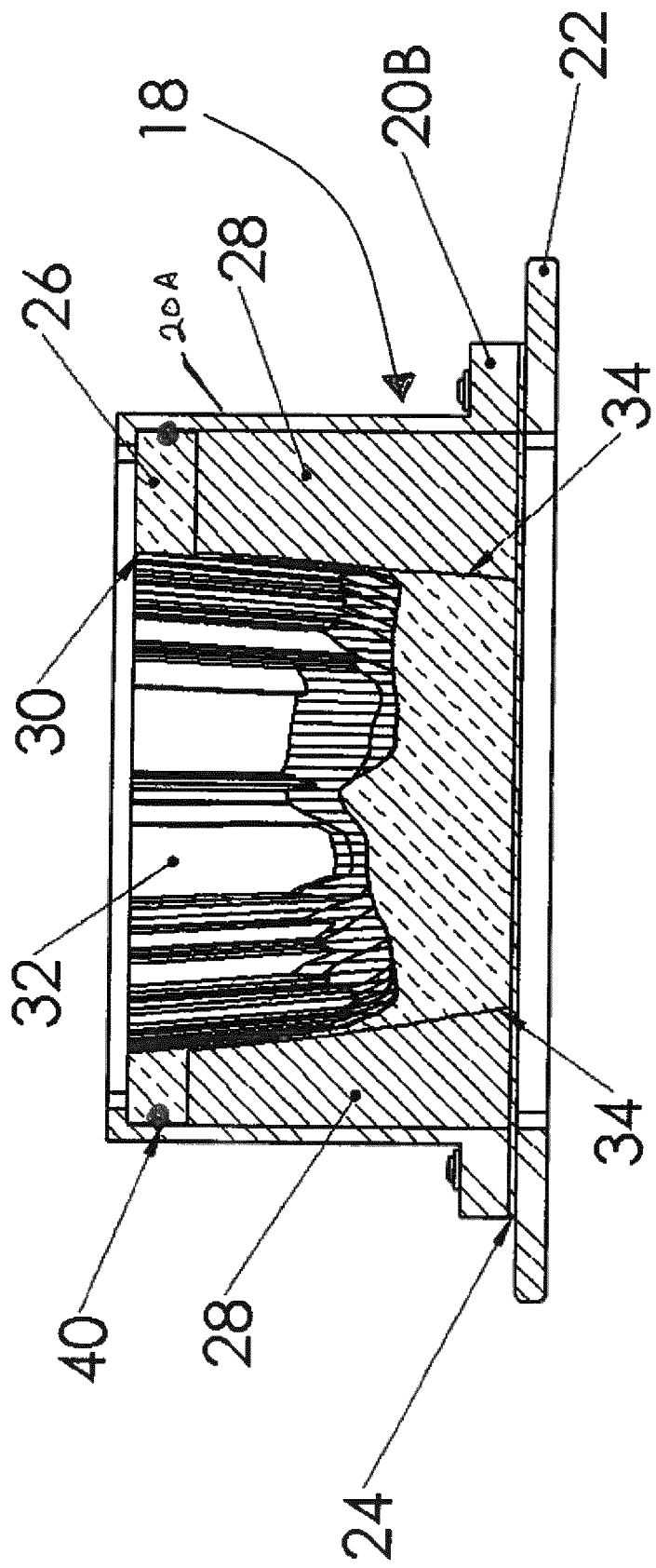
Figure 10E:
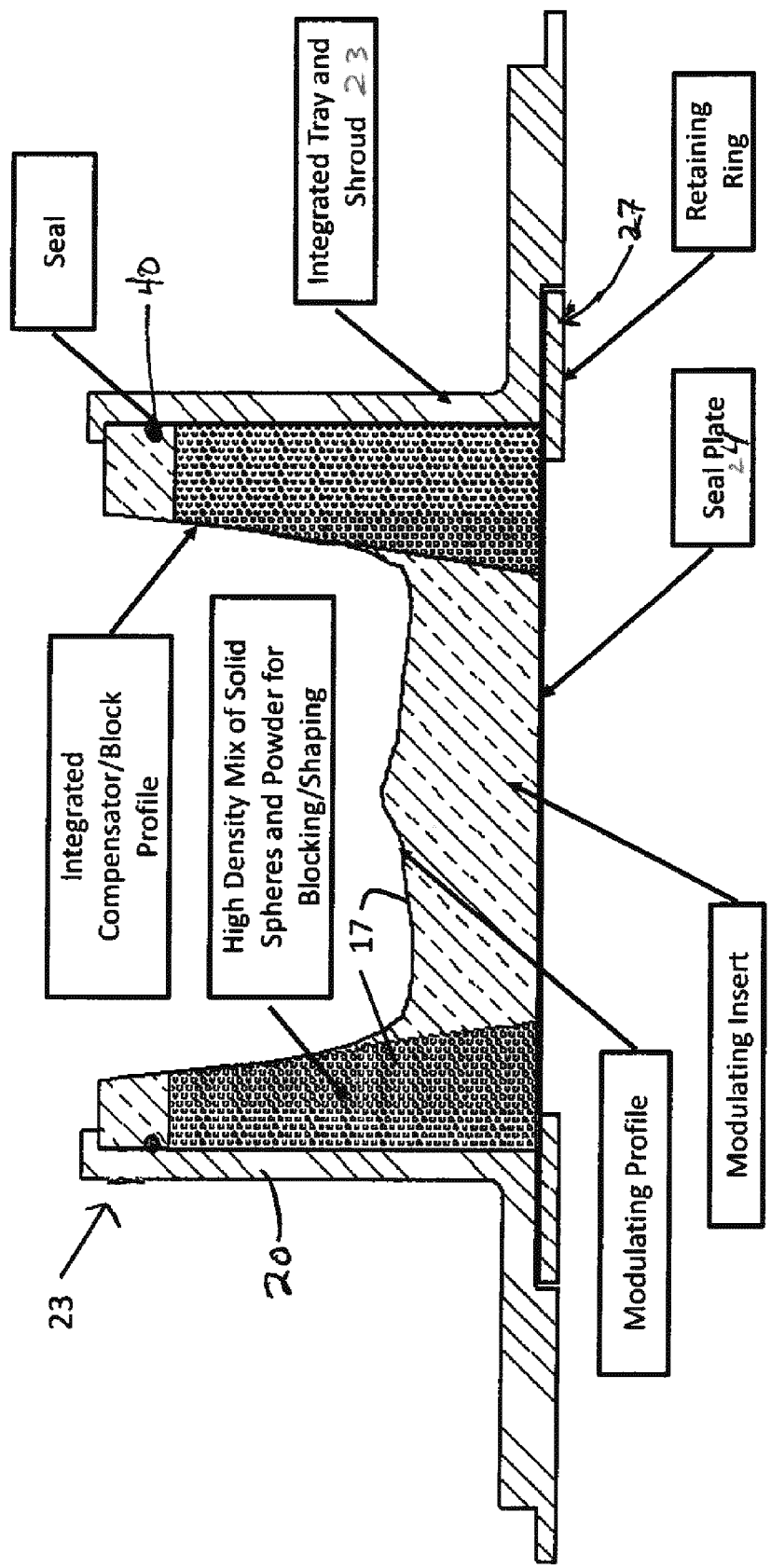
Figure 11A:
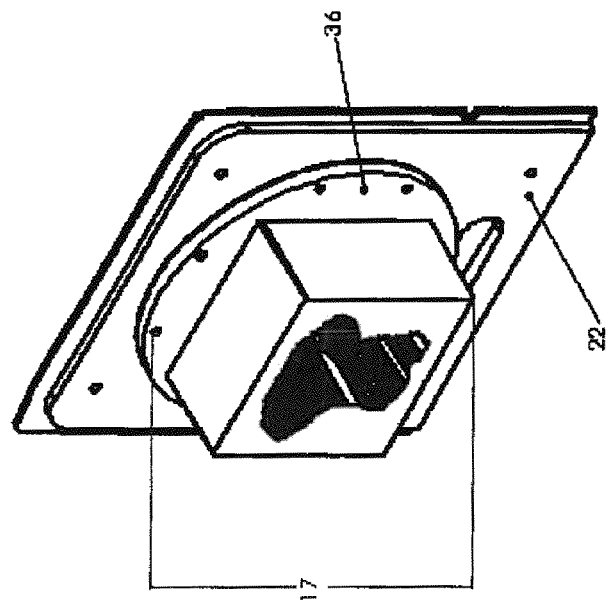
FIGS. 11, 11A, 11B, 12, 13, and 14 all illustrate various views of a non-shrouded flanged ISASU.
Figure 11B:
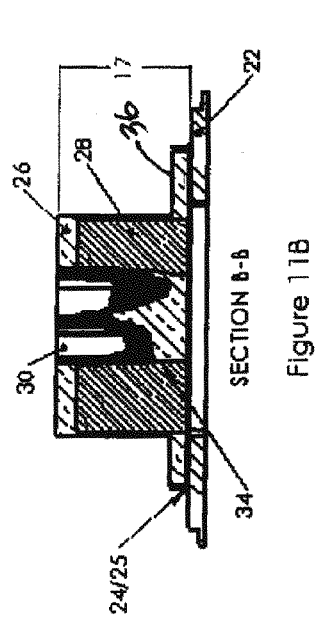
Figure 11:
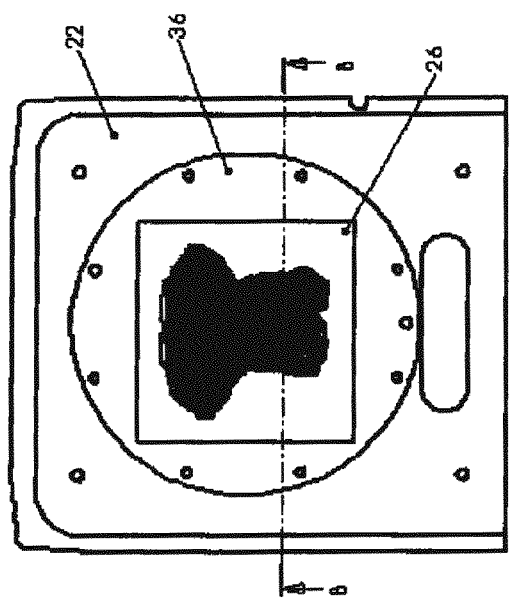
Figure 12:
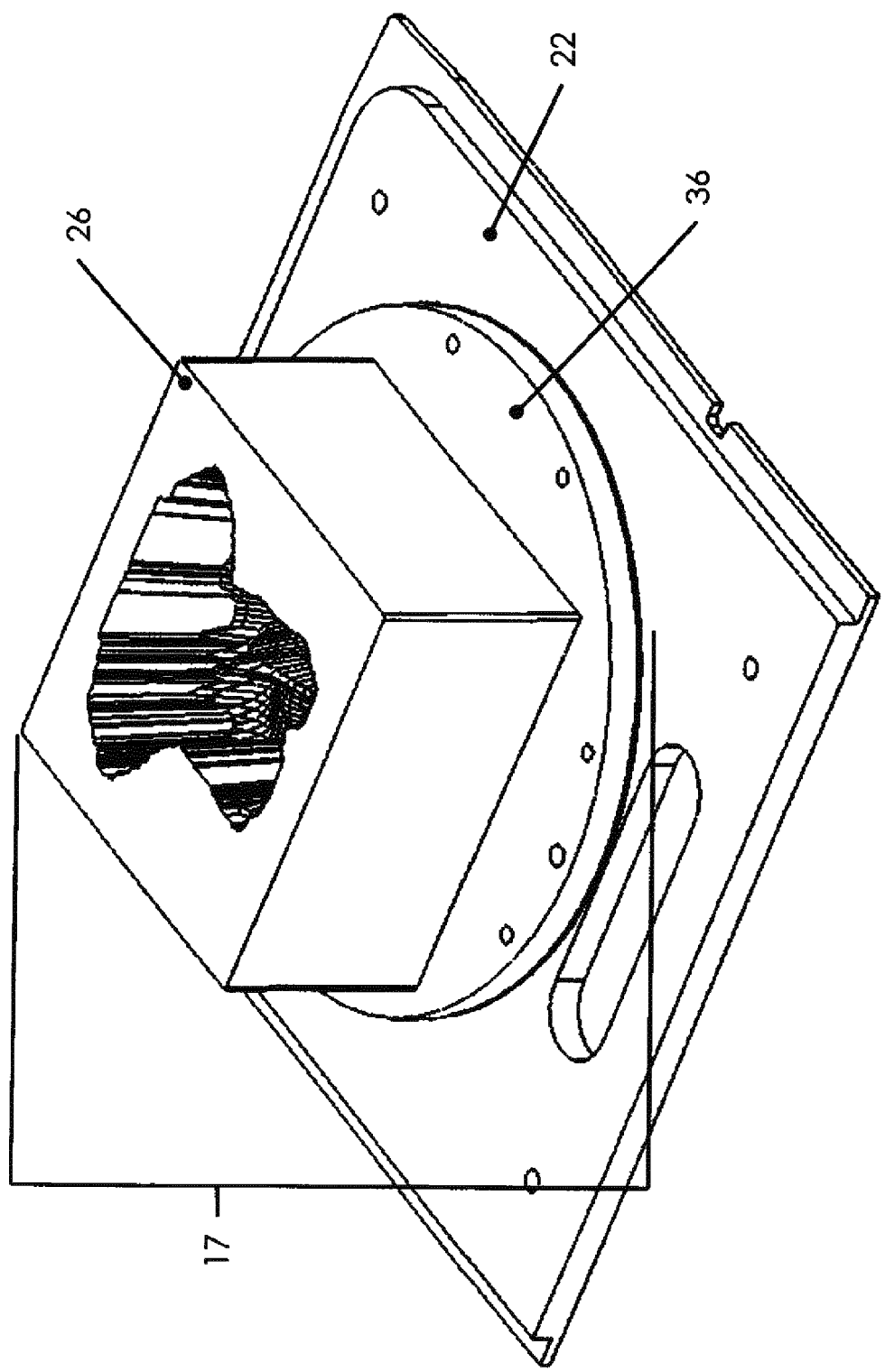

FIG. 8 illustrates that a shroud 20 may include a shroud body 20A, a shroud flange 20B, and a shroud lip 20C. The shroud body is typically dimensioned for close fit to and adjacent the walls of ISASU 17. Shroud flange 20B typically engages the shroud body opposite from lip 20C with shroud flange 20B extending laterally for flush relation with tray 22 and fastened thereto by conventional fasteners. FIGS. 9 and 10 illustrate that a gasket or O-ring 40 may be provided for seal between a machined acrylic shroud or other shroud and the ISASU 17. Typically, gasket 40 will provide a seal between exterior walls defining sculpting portion 26 and inner walls of shroud body 20A. Lip 20C projects inwardly and provides support to ISASU 17, when the tray is mounted in the LINAC. Seal 24 (full 24, FIG. 10 or partial 25, FIG. 18) may be provided between ISASU 17 and the tray 22. Shroud 20 may include, in place of lip 20C, a substantially complete bottom wall.

Additional views are provided in FIGS. 9 and 10, including further details showing the use of tray 22 having, optionally, a tray cutout 22A where the cutout will be typically dimensioned so that exposure of tray 22 to the radiation beam passing the jaws of the LINAC machine is substantially avoided. Seal 24 may be reusable, as would tray 22. Likewise, gasket seal 40 may be reusable as would the shroud 20. Further, sculpting material or shaping portion material 28 may be reusable, such as a tungsten powder or slurry or other suitable material. In such a manner, tungsten, an expensive material, or other shaping material could be easily recycled.

FIGS. 10A-10E illustrate an integrated shroud/tray unit 23 wherein the ISASU 17, typically without a flange, is adapted to fit with the shroud 20 of the one-piece shroud/tray unit 23. Retainer ring 27 (FIG. 10E) may be used, optionally, in coordination with fastener to retain ISASU 17 within the shroud/tray unit 23.

FIGS. 11, 11A, 11B, 12, 13, and 14 illustrate an embodiment of Applicant's ISASU 17, which incorporates an integral flange 36 adjacent the body portion thereof. While similar to the concepts set forth and devices set forth hereinabove, the embodiment shown in these Figures utilizes a flange.

Figure 13:
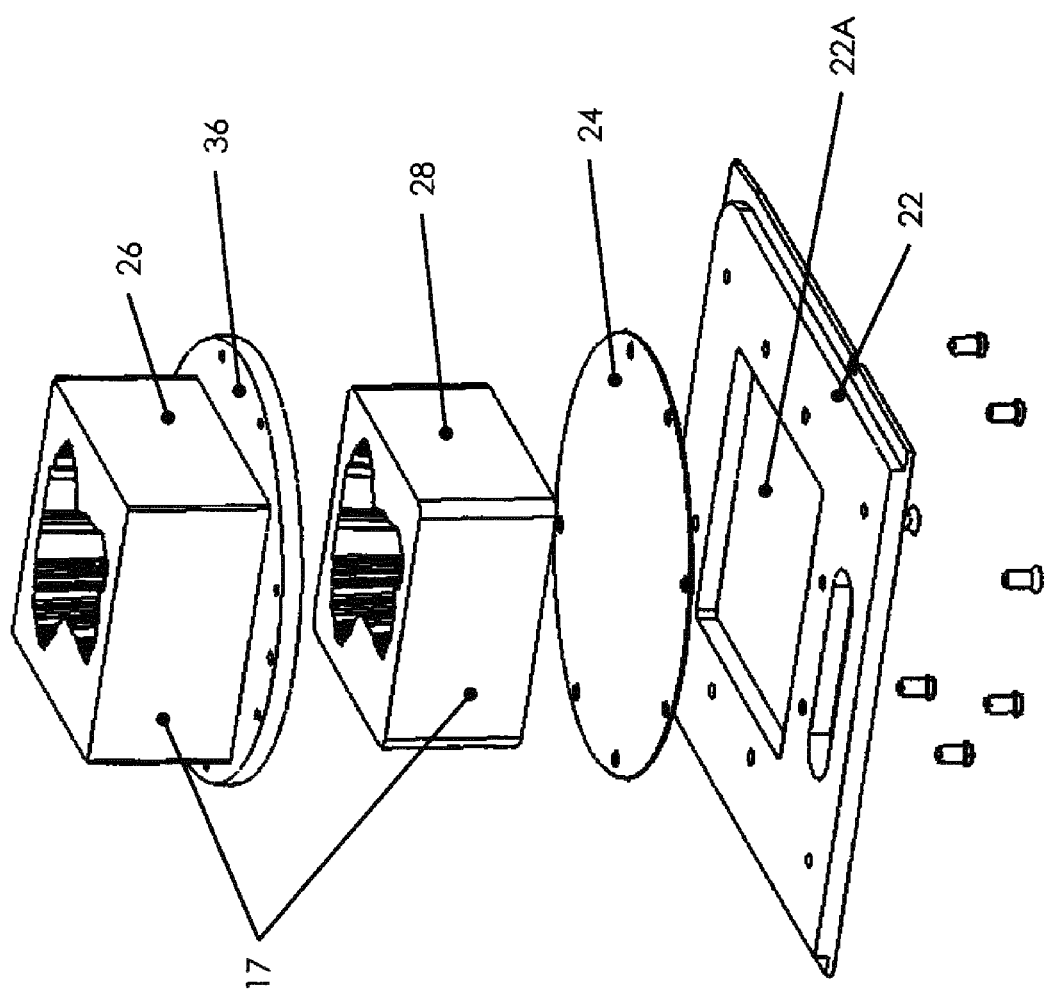
Figure 14:
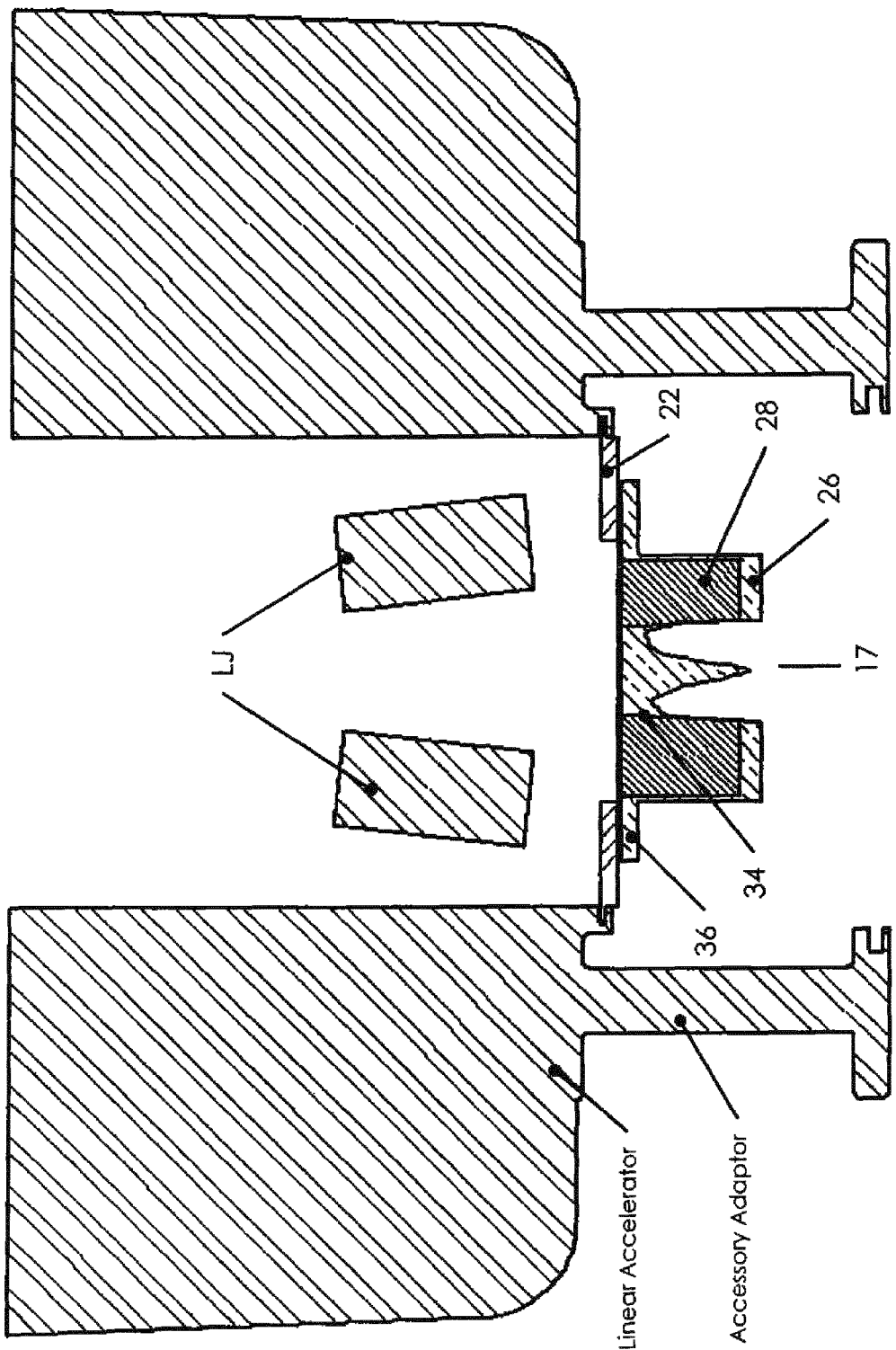

However, Applicant utilizes flange 36 in conjunction with a unitized structure 17 defining shaping portion walls 34 and sculpting portion cavity 32 having shaped walls 30 therein. As seen in FIG. 13, flange 36 is typically provided integral with and typically may be made from sculpting portion material 26. A cavity at least partially within said sculpting portion material 26 may define shaping portion walls 34 as seen in FIG. 14 and at least partially filled with a shielding/beam shaping material which may be solid, liquid, powder, granular media and is typically denser than the compensator material (tungsten, lead, Cerrobend, etc.). Seal plate 24 may be used between tray 22 and ISASU 17 to help prevent leakage or movement.

ISASU 17 may come in different sizes, typically 3, 4, 5, 6, 7, 8 inch and up to 12 inches (measured across the widest portion as dictated by the tumor size. Typically the exterior shape may be cylindrical or rectangular. The smallest size would be used for a given tumor size.

Figure 15:
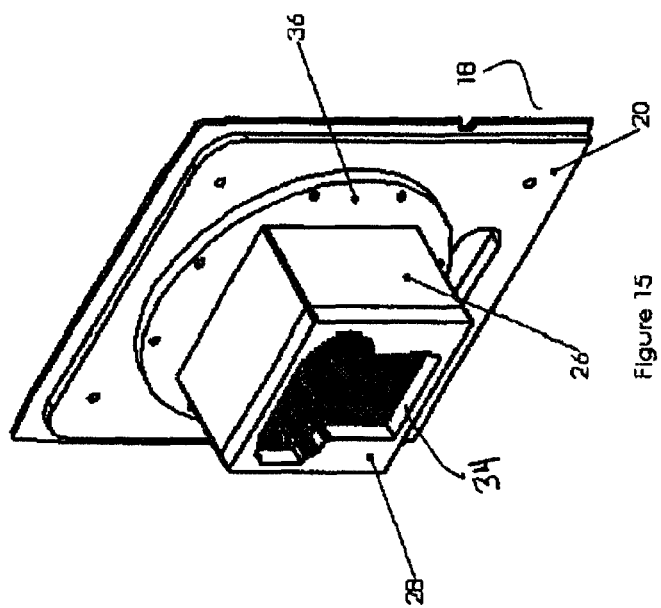
FIGS. 15, 15A, 15B, and 15C illustrate an embodiment of a capped ISASU.
Figure 15C:
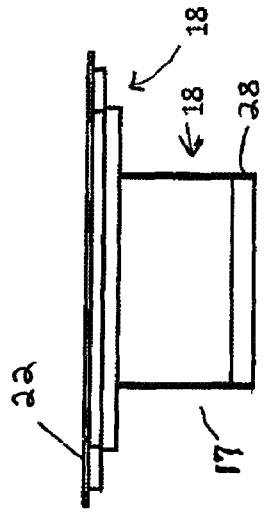
Figure 15B:
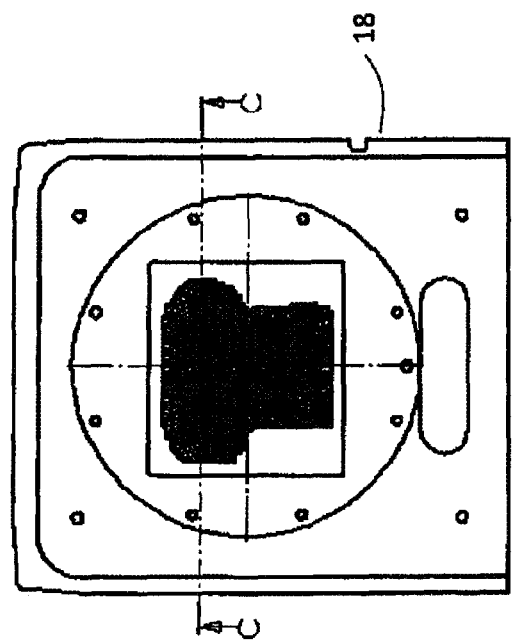
Figure 15A:
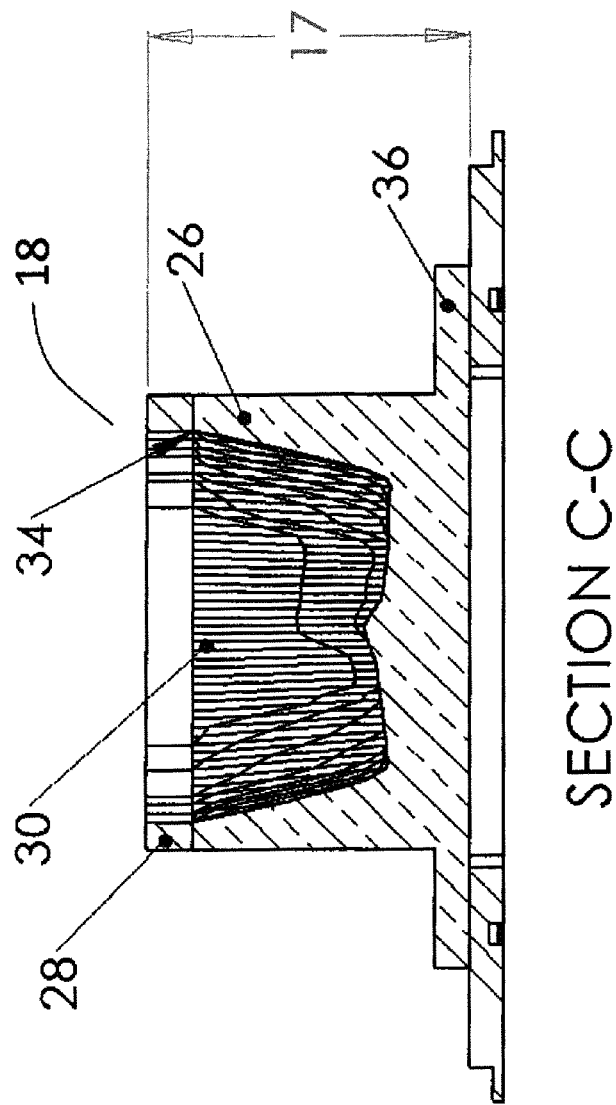
Figure 17:
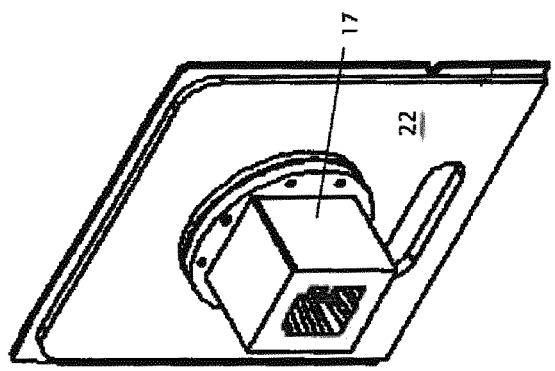
FIGS. 17, 17A, 17B, 17C, and 18 illustrate an embodiment of a capped ISASU.
Figure 17C:
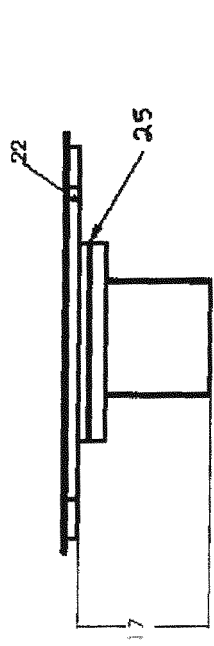
Figure 17B:
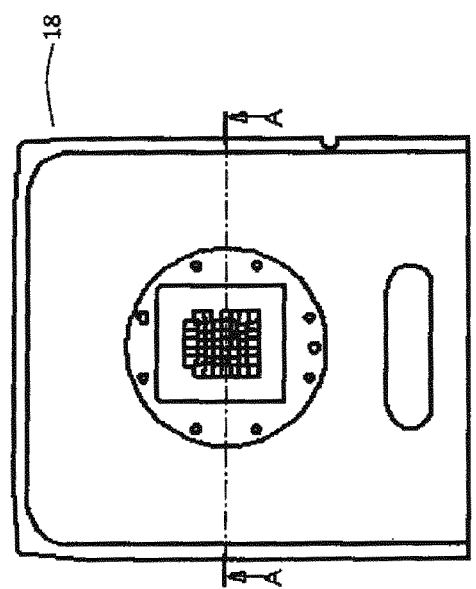
Figure 17A:
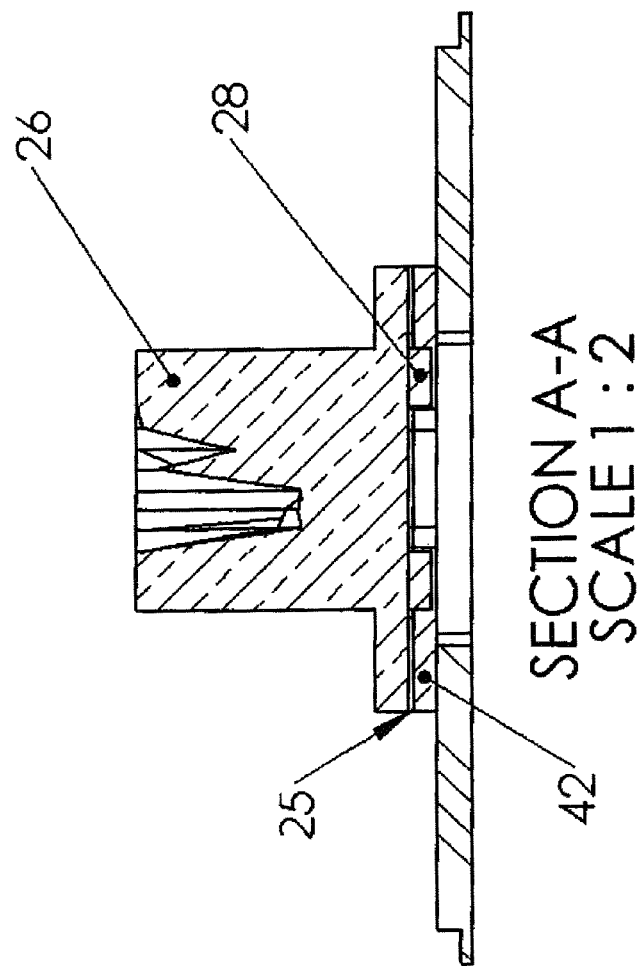

FIGS. 15, 15A, 15B, and 15C illustrate an alternate preferred embodiment of Applicant's ISASU 17, wherein shaping portion material 28 is substantially downstream (when the tray is mounted normally in the head) from sculpting portion material 26, yet integral therewith fastened as by fasteners known in the trade or by an appropriate adhesive such that it is integral with, registered to and typically has walls joining walls of shaping portion material 28. When so joined, the through profile may have shaping portion walls 34 typically flush with and represent an extension of milled walls 30, at their removed perimeters or staggered inward as seen in FIG. 3. Shaping portion walls 34 would typically diverge slightly (for example, seen in the cross-sectional view in FIGS. 16, 16A, 16B, and 16C), but may be angled or straight. Wherein such an embodiment of the ISASU 17 is presented, sometimes here referred to as a "capped" ISASU 17, it may be shrouded or used a flange 36, as illustrated in FIGS. 15-15C. When flanged, some attachment means may be provided for engagement of sculpting portion material 26 to shaping portion material 28. When shrouded, it may, optionally, not be necessary as the shroud itself and the lip or wall would provide the proper register of positional placement of the two materials. Typically, this embodiment seal 24 would not be necessary. It is noted that the tray may be mounted on the LINAC machine so the ISASU 17 is directed towards or away (tray reversed 180 degrees in slots) from the patient.

Turning to FIGS. 16-16C, general ISASU 17 construction may be noted. Specifically, flanged ISASU 17 may come in a standardized set of sizes, wherein the rectangular or body portion of the ISASU may come in standardized sizes and the flanged portion may have a standardized or variable fastener pattern. The choice of the standardized size would be dependent on the prescribed treatment, dosage, and tumor characteristics.

Moreover, FIGS. 16-16C show the straight, tapered, angled or diverging shaping portion walls 34 defining an inner profile of the cavity provided for shaping portion material 28 to be inserted, placed, cast or otherwise provided therein. It will be noted with respect to FIGS. 16-16C that projecting the shaping portion walls will typically join up downstream or downstream to the edge of the profile of milled walls 30 at the furthest most portion thereof, or a staggered arrangement may be provided.

Although not illustrated, a capped type shaping portion material 28 as seen on FIGS. 15-15C, may be utilized with the embodiment seen in FIGS. 16-16C, such that there is shaping and shaping material (and walls 34) at least partially upstream and at least partially downstream of the sculpting material in an integral ISASU 17.

FIGS. 17, 17A, 17B, 17C, and 18 illustrate a preferred embodiment of Applicant's ISASU 17, wherein a solid blank 42 of sculpting material is milled with a cavity for shielding (shaping) material 28 and milled with boundaries (walls) of the sculpting material defining the through profile of the shaping material. In this embodiment, a blank 42 is placed substantially adjacent sculpting portion material 26.

Figure 18:
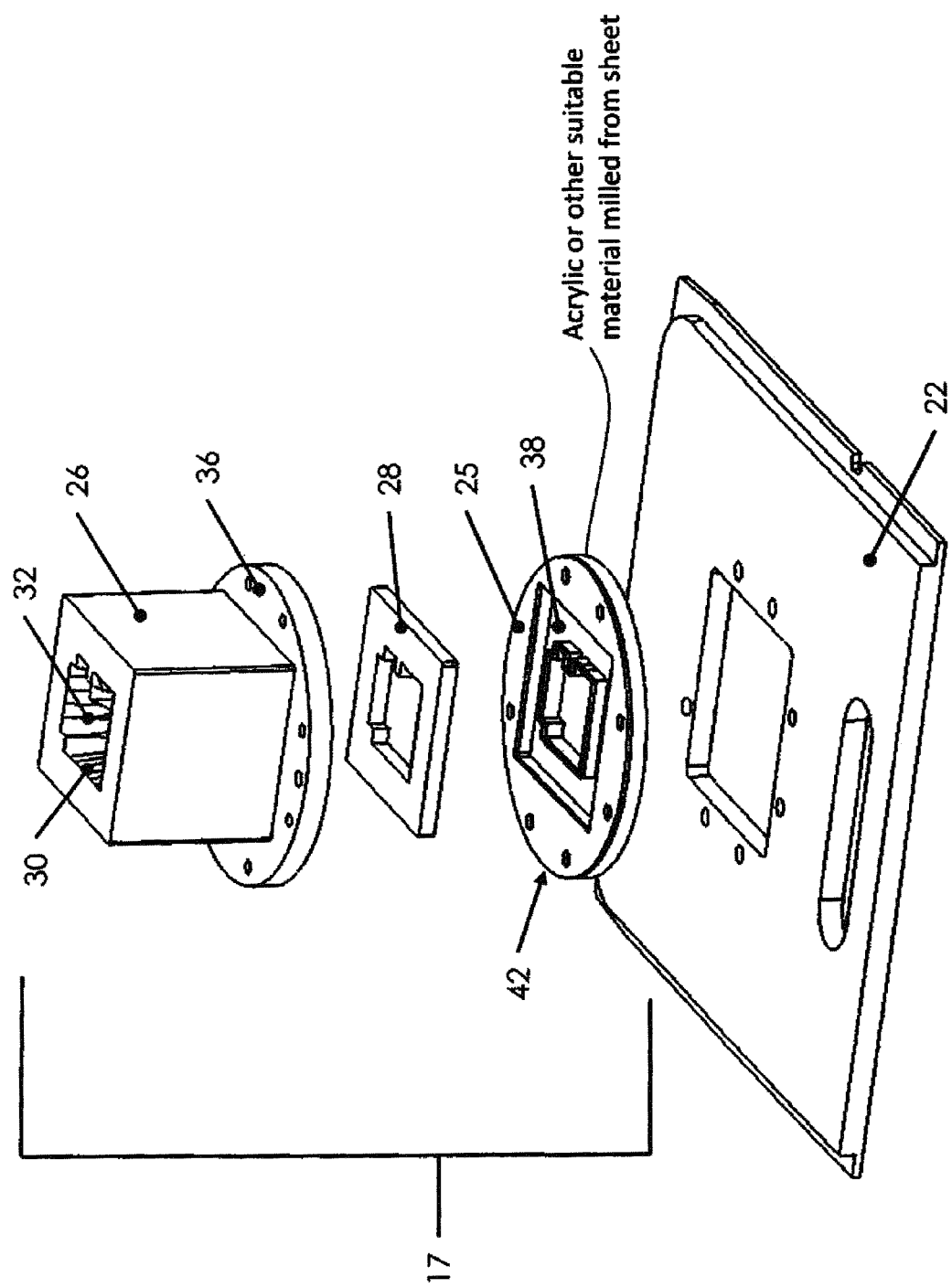
Figure 19:
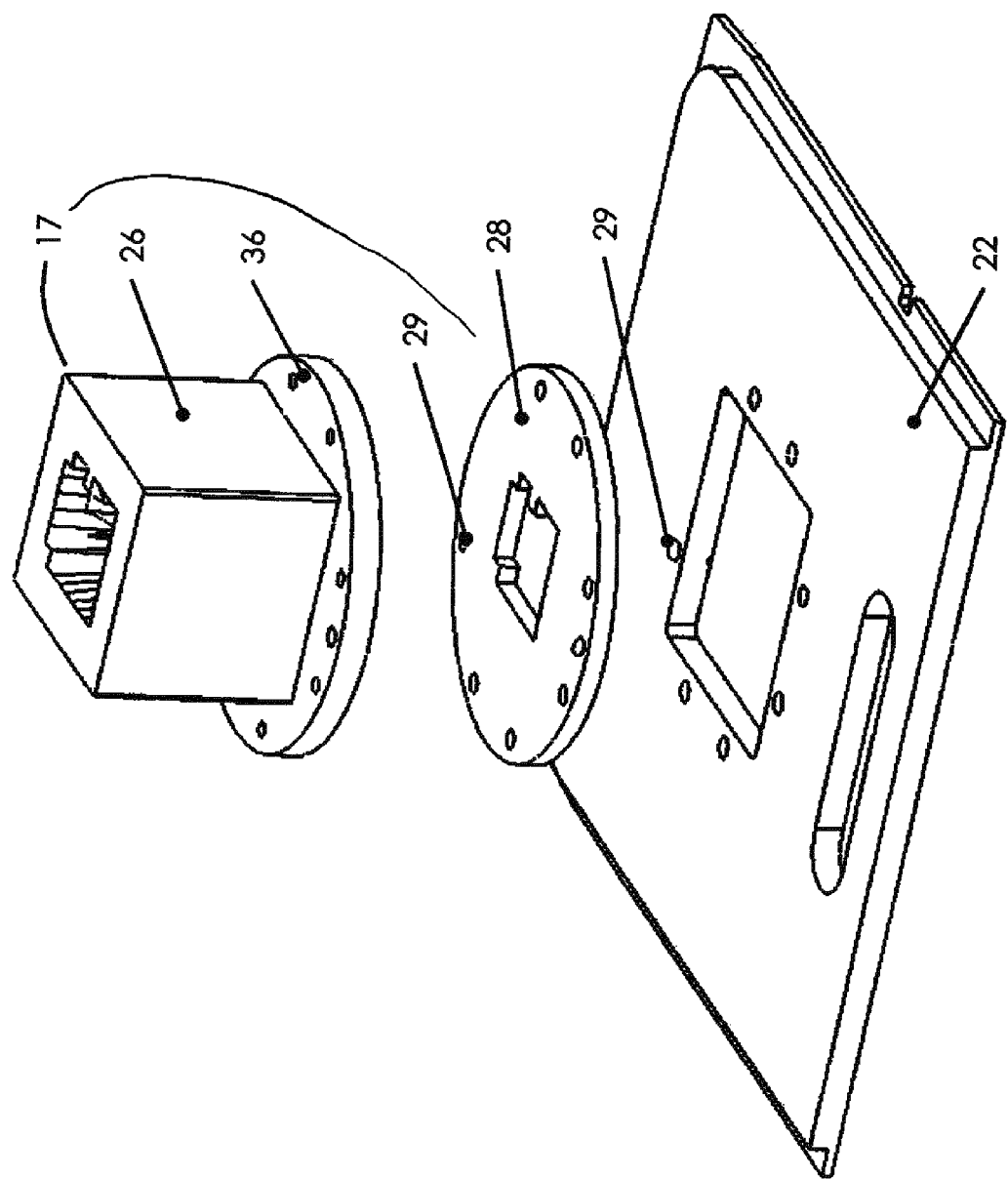
FIGS. 19, 20, 20A, 20B, and 20C illustrate views of an alternate preferred embodiment of Applicant's ISASU featuring a solid shaping portion material 28 upstream of a compensator portion comprising sculpting portion material.
Figure 20:
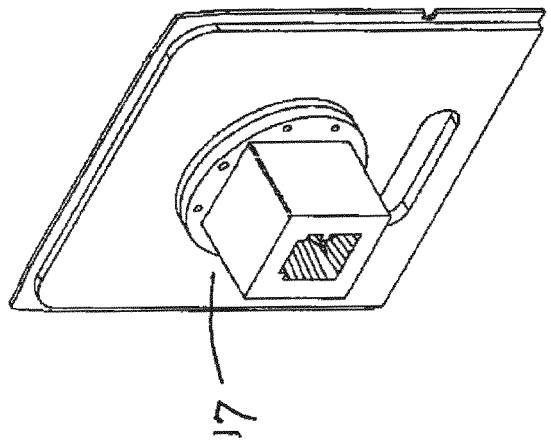
Figure 20A:
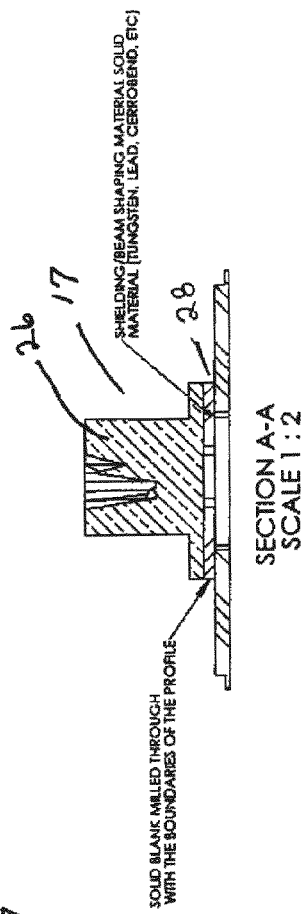
Figure 20C:
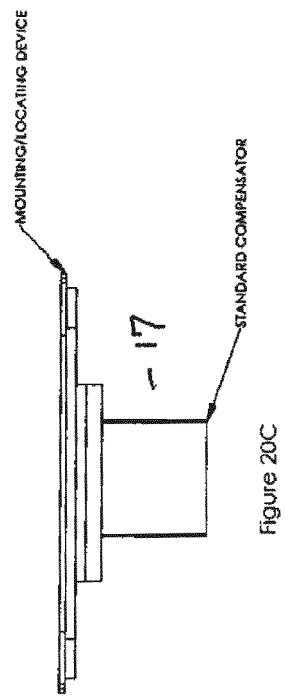
Figure 20B:
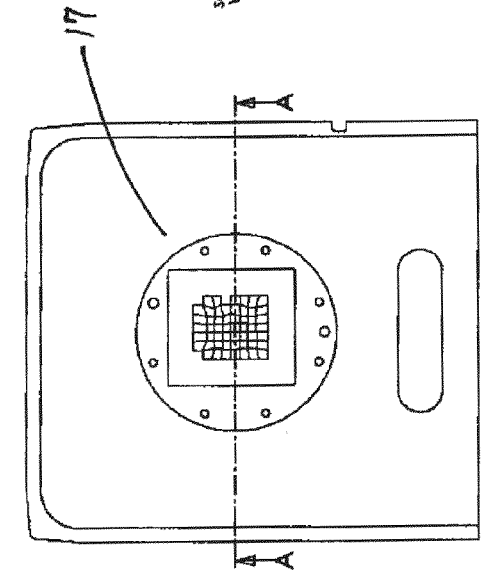
Figure 22:
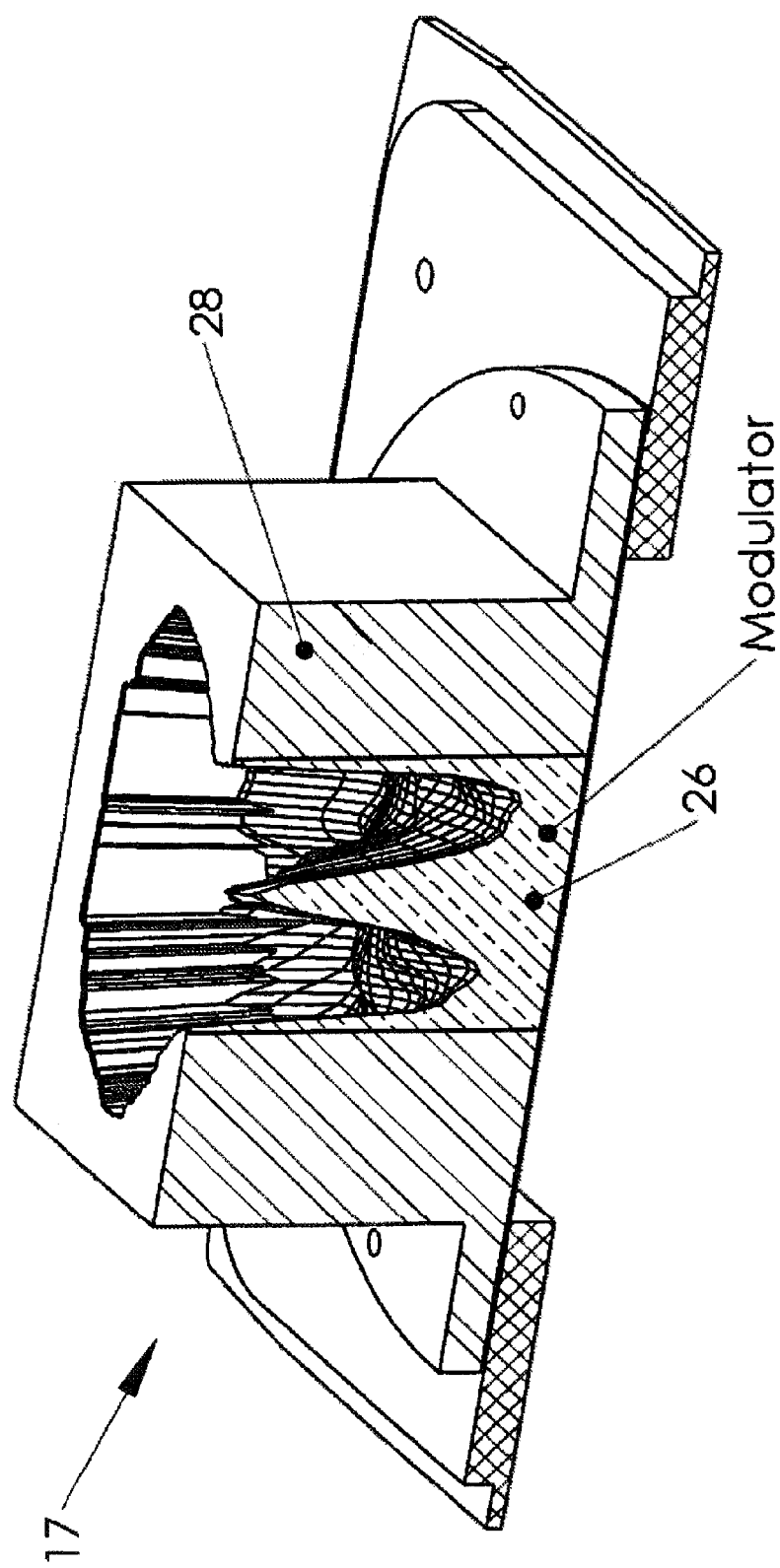
FIG. 22, 22A-22C illustrate an alternate preferred embodiment of Applicants' device.
Figure 22A:
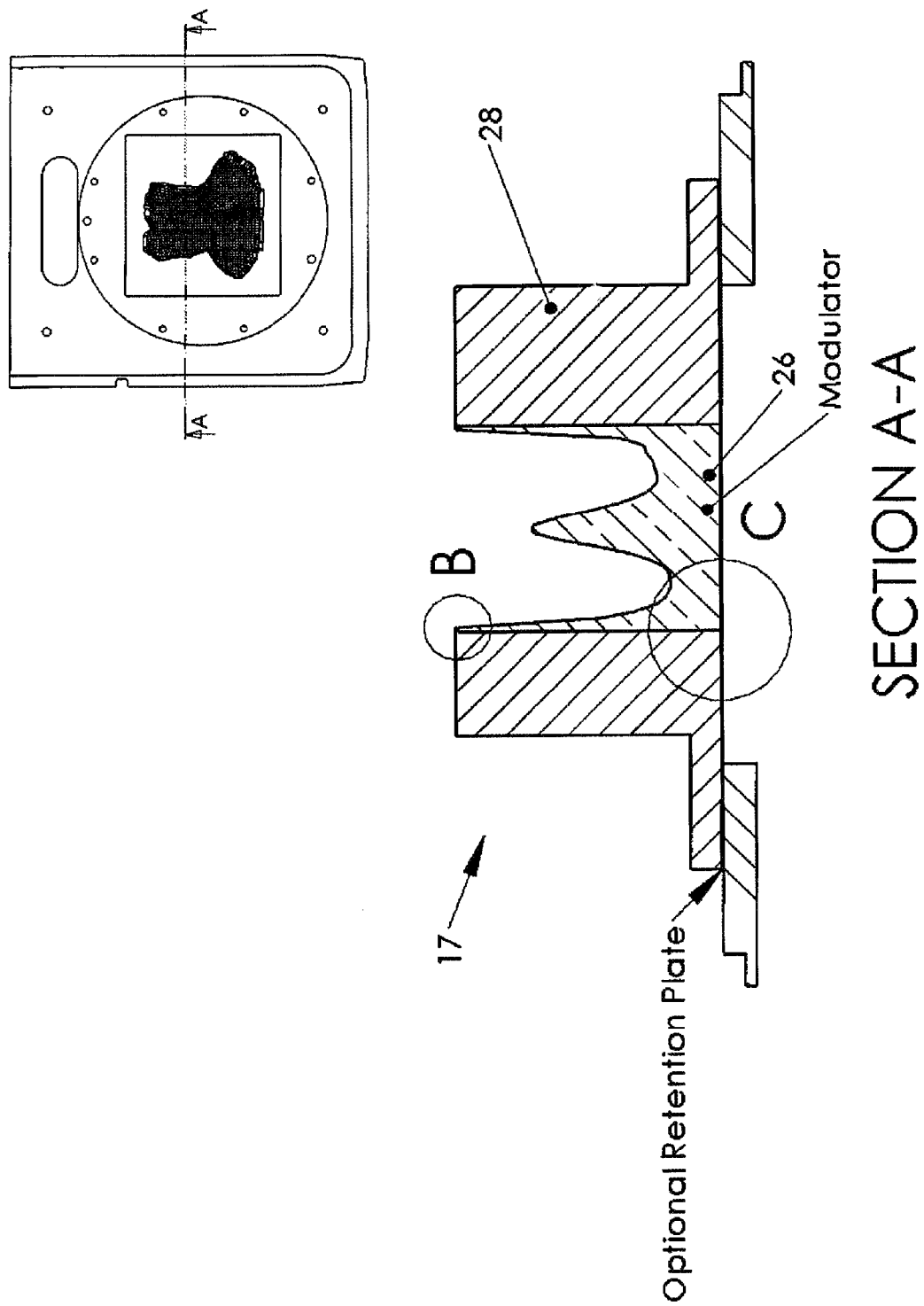
Figure 22B:
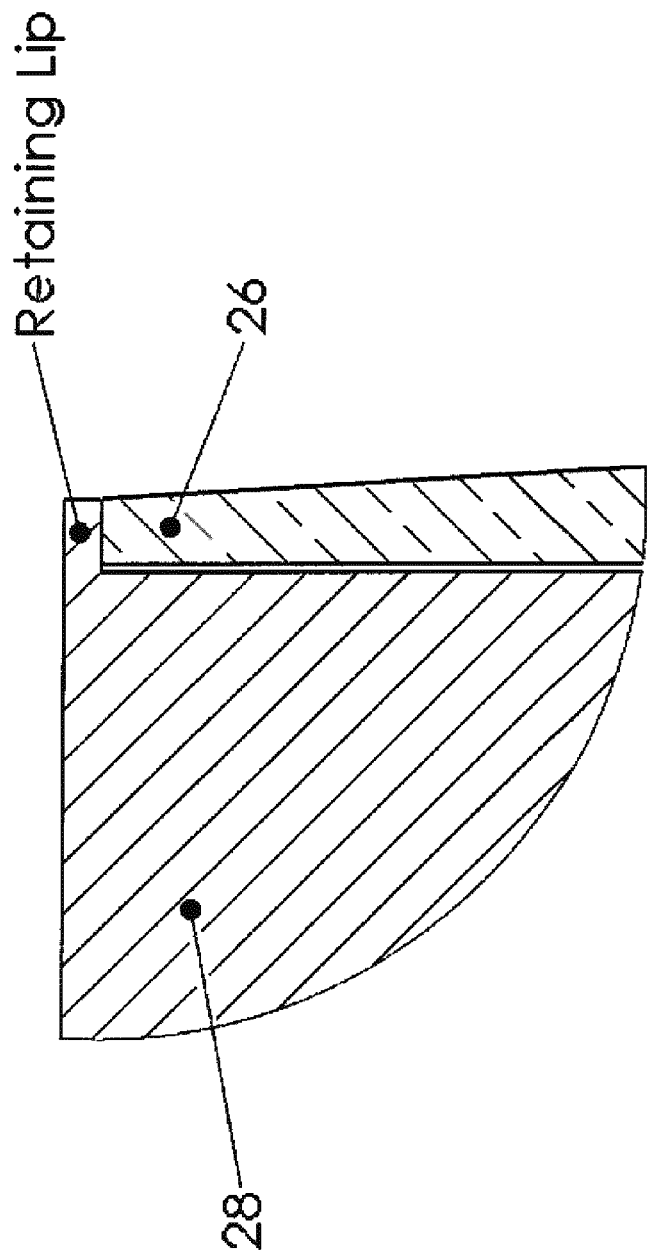
Figure 22C:
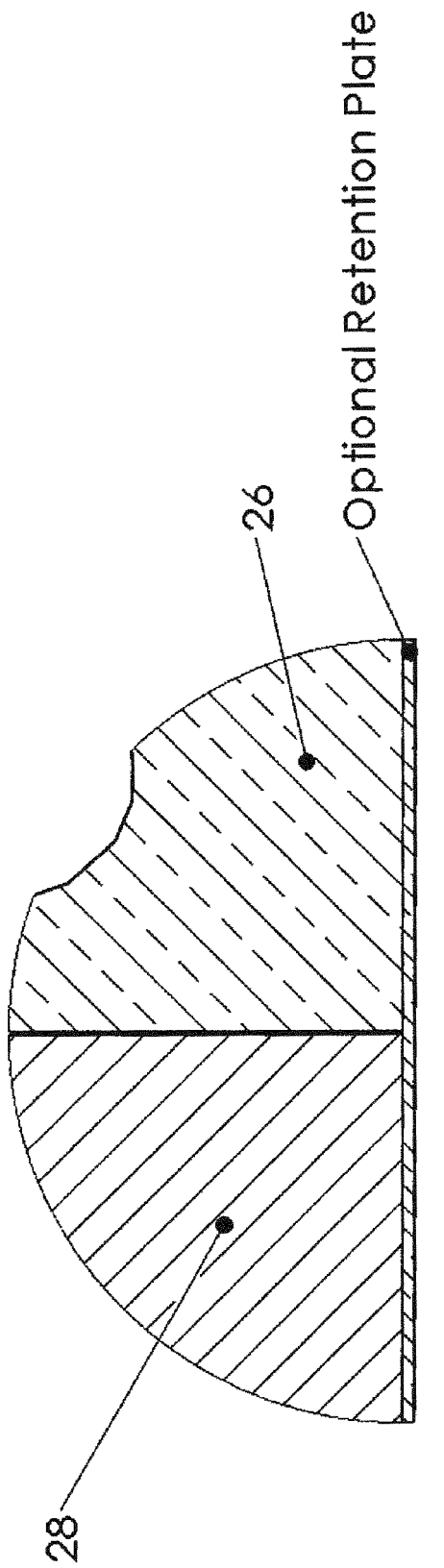

As seen in FIG. 18, the same variation of a capped ISASU 17 is seen to have a solid blank 42, such as acrylic or other material, milled with a cavity 38 and provided optionally with a seal 25 (partial). A solid, liquid, powder, granule, slurry or other suitable media type of appropriate shaping material 28 is provided for insertion or placement in cavity 38 of solid blank 42, typically engaged with sculpting portion 26. Engagement may be provided between blank 42 and sculpting portion material 26 as by engagement of flange 36 and fasteners engageable thereto with fastener holes on blank 42 and fastener holes on tray 22. Again, ISASU 17 is a integral unit as in the earlier embodiments.

FIGS. 19, 20, 20A, 20B, and 20C illustrate an alternate preferred embodiment of Applicant's invention. This uses an appropriately shaped shaping portion material 28 engaged to sculpting portion material 26 having flange 36 thereon. Shaping portion has a fastener pattern that matches that of the flange and tray. The pattern as in previous embodiments may be asymmetrical (see where holes 29 match up) so that the two portions of the ISASU 17 may be registered properly one to the other and then registered properly to the tray 22.

Applicants' invention provides an integrated shaper and sculpting unit which differs from the prior art separate units. There are known prior art methods of determining the through profile of a block, such as a Cerrobend block that is used for shaping the beam. There are also known ways of milling a compensator, for example, a brass compensator, so that the three dimensional surfaces within the sculpturing profile comply with the treatment plan.

In one embodiment of Applicants' present invention, for example, see FIG. 5, the blocking or shaping material will be adjacent the near surface or end 17a of the sculpting material. In such a case, points that define the through profile of the standard block are scaled with respect to beam divergence up into the integrated unit. The scaling of the through profile of the compensator when it is moved up into the ISASU 17 is such that the beam is shaped downstream so it falls where the separate block of the through profile would have been placed downstream, such as in a standard separate, spaced apart prior art compensator and block. That is to say, the walls defining the through profile of the block are scaled upstream into the ISASU 17. Moreover, the end profile for that outline defining the removed surface of a separate compensator may be shrunk by an amount generally equal to the gap between the through profile of the separate block and the removed end 17b profile of the compensator, as found in the software program that would define the two units prepared separately as known in the prior art.

FIG. 21 illustrates a manner in which sculpting and shaping portions of the ISASU 17 may be located. In this illustration, it is seen that the through profile of the block, when the block is combined with the compensator, may be scaled back typically from 100 cm SSD (or any other standard or desired reference) as illustrated. FIG. 21 shows the manner of scaling back to provide a shaping profile for integration into or onto the sculpting material, taking into account beam divergence.

FIGS. 22, 22A-22C illustrate the ISASU 17 may include a solid shaping material 28 defining walls including both the shaping profile and a housing for receiving a sculpting material 26.

In any embodiment of Applicants' device wherein a shaping cavity is provided, and filled with a shaping material, such as a fluid, the material may be substantially sealed in the cavity with the use of a foam, such as a medium density foam pressed into the at least partially filled shaping cavity, to help prevent movement or leakage of the fluid, especially when the LINAC head is rotated.

Some of the enclosed embodiments illustrate the use of a conventional compensator, flanged, with an additional blocker (to shape the beam) comprising a different, typically higher density material, set forth herein. Yet the conventional compensator modified would have the integrated blocking material, properly shaped, either within the walls thereof, or capped at either or both ends, as has have been set forth herein poured or otherwise sealed, and the tray may be mounted with the removed end towards or away from the patient.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. An apparatus for engagement with a LINAC head of a LINAC machine, the head having an engagement member for IMRT of a cancer patient, the apparatus comprising:
    a first member comprising a first material, the first material having beam shaping properties and a second material, the second material having beam sculpting properties, at least some of the first material and some of the second material laying flush to one another;
    a second member, the second member adapted to engage the first member such that the second member including walls adapted to removably engage the engagement member of the LINAC head of the LINAC machine so as to place the first member in a radiation beam, such that the beam passing through the first member is both shaped and sculpted.

2. The apparatus of claim 1, wherein the first member includes walls defining a shaping cavity, wherein at least some of the walls defining a shaping cavity are comprised of the second material, and wherein at least some of the walls of the shaping cavity substantially define a shaping profile.

3. The apparatus of claim 2, wherein the shaping cavity contains the first material and wherein the first material is a fluid.

4. The apparatus of claim 3, wherein the fluid is one of the following: tungsten, a tungsten binder mix, a ferrous and resin mix, or Cerrobend.

5. The apparatus of claim 2 wherein the first material is one of the following: tungsten (solid, powder, shot, tungsten shot and tungsten powder mixture, liquid or in slurry form), lead and/or Cerrobend (solid, powder, powder/solid shot mixture or liquid form or any other suitable dense material or mixture thereof (solid, solid/powder, shot/powder).

6. The apparatus of claim 5, wherein the first material has a density of between about 2.5 and about 20 grams/cubic centimeter.

7. The apparatus of claim 1, wherein the second member includes a tray and wherein the first member is engaged to the tray, the tray adapted to engage the head of a LINAC.

8. The apparatus of claim 7, wherein the first member includes a flange.

9. The apparatus of claim 8, wherein the flange is made at least partially from the second material.

10. The apparatus of claim 1, further including a tray, the tray adapted to engage the head of a LINAC, wherein the first member includes a flange, wherein the flange is adapted to engage the tray.

11. The apparatus of claim 10, wherein the flange is made at least partially from the shaping material.

12. The apparatus of claim 1, wherein the first material is one of a solid, liquid, powder, granular, shot, slurry or mix.

13. The apparatus of claim 1, wherein the second member includes a shroud, and the tray.

14. The apparatus of claim 13, wherein the shroud is made from acrylic or polycarbonate.

15. The apparatus of claim 3, further including a seal plate adapted to engage the first member to seal the shaping cavity.

16. The apparatus of claim 1, wherein the second material is solid and includes walls defining a sculpting profile and the first material is solid and contains walls defining a shaping profile.

17. The apparatus of claim 16, the second member further including a tray, wherein the first or second material is removably located substantially adjacent the tray, the tray adapted to engage the LINAC head.

18. The apparatus of claim 1, wherein the first member has external walls that are substantially cylindrical.

19. The apparatus of claim 1, wherein the first member has external walls that are substantially rectangular.

20. The apparatus of claim 1, wherein the second member further includes an integrated shroud/tray for engagement of the member to the LINAC head.

21. An apparatus for engagement with a LINAC head of a LINAC machine, the head having an engagement member, for IMRT of a cancer patient, the apparatus comprising:

a first member incorporating integrating both a first material and a second material, the member for placement in the LINAC head for modification of the IMRT beam;

wherein the first member includes walls defining a shaping cavity, wherein at least some of the walls defining a shaping cavity are comprised of the second material, and wherein at least some of the walls of the shaping cavity substantially define a shaping profile; wherein the shaping cavity contains the first material and wherein the first material is a fluid;

wherein the first material has a density of between about 2.5 and about 20 grams/cubic centimeter;

further including a tray and wherein the first member is engaged to the tray, the tray adapted to engage the head of a LINAC; and further including a seal plate adapted to engage the first member to substantially seal the fluid in the shaping cavity.

22. A method of treating a cancer patient with IMRT, the method comprising:

providing a first member comprising a first material the first material having beam shaping properties and a second material, the second material having beam sculpting properties, at least some of the first material and some of the second material laying flush to one another;

a second member, the second member adapted to engage the first member such that the second member including walls adapted to removably engage the engagement member of the LINAC head of the LINAC machine so as to place the first member in a radiation beam, such that the beam passing through the first member is both shaped and sculpted; and irradiation of a tumor in a cancer patient wherein the radiation beam is modified by engagement of an integrated member with the LINAC head, the member incorporating both the first material and the second material.

* * * * *